(12) United States Patent
Yu et al.

(10) Patent No.: US 7,858,083 B2
(45) Date of Patent: *Dec. 28, 2010

(54) PAN CANCER ONCOLYTIC VECTORS AND METHODS OF USE THEREOF

(75) Inventors: DeChao Yu, Palo Alto, CA (US); Yuanhao Li, Palo Alto, CA (US)

(73) Assignee: BioSante Pharmaceuticals, Inc., Lincolnshire, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/327,936

(22) Filed: Dec. 4, 2008

(65) Prior Publication Data

US 2009/0099125 A1 Apr. 16, 2009

Related U.S. Application Data

(62) Division of application No. 11/074,694, filed on Mar. 9, 2005, now Pat. No. 7,473,418.

(60) Provisional application No. 60/556,549, filed on Mar. 25, 2004.

(51) Int. Cl.
*A01N 63/00* (2006.01)
*A01N 43/04* (2006.01)
*A61K 48/00* (2006.01)
*C07H 21/02* (2006.01)
*C07H 21/04* (2006.01)

(52) U.S. Cl. ............... 424/93.2; 424/93.21; 536/23.1
(58) Field of Classification Search ............. 424/93.2
See application file for complete search history.

(56) References Cited

U.S. PATENT DOCUMENTS

| | | | |
|---|---|---|---|
| 5,543,328 A | 8/1996 | McClelland et al. |
| 5,677,178 A | 10/1997 | McCormick |
| 5,698,443 A | 12/1997 | Henderson et al. |
| 5,731,190 A | 3/1998 | Wickham et al. |
| 5,756,086 A | 5/1998 | McClelland et al. |
| 5,801,029 A | 9/1998 | McCormick |
| 5,846,782 A | 12/1998 | Wickham et al. |
| 5,863,765 A | 1/1999 | Berry et al. |
| 5,871,726 A | 2/1999 | Henderson et al. |
| 5,922,315 A | 7/1999 | Roy |
| 5,962,311 A | 10/1999 | Wickham et al. |
| 5,994,128 A | 11/1999 | Fallaux et al. |
| 5,998,205 A | 12/1999 | Hallenbeck et al. |
| 6,033,908 A | 3/2000 | Bout et al. |
| 6,057,155 A | 5/2000 | Wickham et al. |
| 6,127,525 A | 10/2000 | Crystal et al. |
| 6,140,087 A | 10/2000 | Graham et al. |
| 6,153,435 A | 11/2000 | Crystal et al. |
| 6,432,700 B1 | 8/2002 | Henderson et al. |
| 6,455,314 B1 | 9/2002 | Wickham et al. |
| 6,495,130 B1 | 12/2002 | Henderson et al. |
| 6,555,368 B1 | 4/2003 | Curiel |
| 6,683,170 B2 | 1/2004 | Curiel et al. |
| 6,692,736 B2 | 2/2004 | Yu et al. |
| 2001/0053352 A1 | 12/2001 | Yu et al. |
| 2003/0039633 A1 | 2/2003 | Yu et al. |
| 2003/0104624 A1 | 6/2003 | Clarke et al. |
| 2003/0104625 A1 | 6/2003 | Cheng et al. |
| 2003/0215948 A1 | 11/2003 | Kaleko |
| 2005/0095705 A1 | 5/2005 | Kadan |

FOREIGN PATENT DOCUMENTS

| | | |
|---|---|---|
| EP | 0623679 B1 | 6/2003 |
| WO | WO 95/19434 | 7/1995 |
| WO | WO 96/17053 | 6/1996 |
| WO | WO 98/07877 | 2/1998 |
| WO | WO 98/13508 | 4/1998 |
| WO | WO 98/14593 | 4/1998 |
| WO | WO 98/39464 | 9/1998 |
| WO | WO 98/39465 | 9/1998 |
| WO | WO 98/39466 | 9/1998 |
| WO | WO 98/39467 | 9/1998 |
| WO | WO 99/06576 | 2/1999 |
| WO | WO 99/25860 | 5/1999 |
| WO | WO 99/39734 | 8/1999 |
| WO | WO 00/15820 | 3/2000 |
| WO | WO 00/46355 | 8/2000 |
| WO | WO 00/67576 | 11/2000 |
| WO | WO 01/36650 | 5/2001 |
| WO | WO 01/92299 | 12/2001 |
| WO | WO 02/067861 | 9/2002 |
| WO | WO 02/068627 | 9/2002 |
| WO | WO 2004/005511 | 1/2004 |

OTHER PUBLICATIONS

Altschul et al., "Basic Local Alignment Tool", *Journal of Molecular Biology*, 215:403-410 (1990).
Batzer et al., "Enhanced Evolutionary PCR Using Nucleotides with Inosine at the 3'Terminus", *Nucleic Acids Research*, 19(18):5081 (1991).
Chao et al., "Assembly of the Cleavage and Polyadenylation Apparatus Requires About 10 Seconds In Vivo and is Faster for Strong than for Weak Poly(A) Sites", *Molecular and Cellular Biology*, 19(8):5588-5600 (1999).

(Continued)

*Primary Examiner*—Valarie Bertoglio
(74) *Attorney, Agent, or Firm*—Ropes & Gray LLP; James F. Haley, Jr.

(57) ABSTRACT

Replication-competent adenoviral vectors which selectively replicate in cancer cells are provided. The replication-competent viral vectors comprise an E2F responsive promoter and/or a telomerase promoter operatively linked to an adenoviral coding region. The replication-competent adenoviral vectors effectively replicate in a variety of types of cancer cells and find broad utility in the treatment of cancer.

6 Claims, 11 Drawing Sheets

OTHER PUBLICATIONS

Donnelly et al., Analysis of the Apthovirus 2A2B Polyprotein 'Cleavage' Mechanism Indicates Not a Proteolytic Reaction, but a Novel Translational Effect: a Putative Ribosomal 'Skip', *Molecular and Cellular Biology*, 82:1013-1025 (2001).

Duke et al., "Sequence and Structural Elements That Contribute to Efficient Encephalomyocarditis Virus RNA Translation", *Journal of Virology*, 66(3):1602-1609 (1992).

Dyson, "The Regulation of E2F by pRB-Family Proteins", *Genes and Development*, 12:2245-2262 (1998).

Fallaux et al., "New Helper Cells and Matched Early Region 1-Deleted Adenovirus Vectors Prevent Generation of Replication-Competent Adenoviruses", *Human Gene Therapy*, 9:1909-1917 (1998).

Furler et al., Recombinant AAV Vectors Containing the Foot and Mouth Disease Virus 2A.

Sequence Confer Efficient Bicistronic Gene Expression in Cultured Cells and Rat Substantia Nigra Neurons, *Gene Therapy*, 8:864-873 (2001).

Graham et al., "Characteristics of a Human cell Line Transformed by DNA from human Adenovirus Type 5", *J. Gen. Virol.*, 36:59-72 (1977).

Gunes et al., "Expression of the *hTERT* Gene is regulated at the Level of Transcriptional Initiation and Repressed by Mad1", *Cancer Research*, 60:2116-2121 (2000).

Huez et al., "Two Independent Internal Ribosome Entry Sites are Involved in Translation Initiation of Vascular Endothelial Growth Factor mRNA", *Molecular and Cellular Biology*, 18(11):6178-6190 (1998).

Jackson et al, "The novel mechanism of initiation of picornavirus RNA translation," *TIBS*, 15:477-483 (1990).

Jackson et al., "Internal Initiation of Translation in Eukaryotes: The Picornovirus Paradigm and Beyond", *RNA*, 1(10):985-1000 (1995).

Jakubczak et al., "An oncolytic adenovirus selective for retinoblastoma tumor suppressor protein pathway-defective tumors: dependence on E1A, the *E2F-1* promoter, and viral replication for selectivity and efficacy", *Cancer Research*, 63(7):1490-1499 (2003).

Johnson et al., "Selectively Replicating Adenoviruses Targeting Deregulated E2F Activity are Potent, Systemic Antitumor Agents", *Cancer Cell*, 1:325-337, 2002.

Kilian et al., "Isolation of a Candidate Human Telomerase Catalytic Subunit Gene, Which Reveals Complex Splicing Patterns in Different Cell Types", *Human Molecular Genetics*, 6(12):2011-2019 (1997).

Kim et al., "Specific Association of Human Telomerase Activity with Immortal Cells and Cancer", *Science*, 266:2011-2015 (1994).

Kirn et al., "Replicating Viruses as Selective Cancer Therapeutics", *Molecular Medicine Today*, 2(12):519-527 (1996).

Kiyono et al., "Both Rb/p16$^{INK4A}$ Inactivation and Telomerase Activity are Required to Immortalize Human Epithelial Cells", *Nature*, 396:84-88 (1998).

Li et al., "A Hepatocellular Carcinoma-Specific Adenovirus Variant, CV890, Eliminates Distant Human Liver Tumors in Combination with Doxorubicin", *Cancer Research*, 61:6428-6436 (2001).

Li et al., "Dual promoter-controlled oncolytic adenovirus CG5757 has strong tumor selectivity and significant antitumor efficacy in preclinical models," *Clinical Cancer Research*, 11:8845-8855 (2005).

Needleman et al., "A General Method Applicable to the Search for Similarities in the Amino Acid Sequence of Two Proteins", *Journal of Molecular Biology*, 48:443-453 (1970).

Noel et al., "High in vivo production of a model monoclonal antibody on adenoviral gene transfer," *Human Gene Therapy*, 13(12):1483-1493 (2002).

Ohtsuka et al., "An Alternative Approach to Deoxynucleotides as Hybridization Probes by Insertion of Deoxyinosine at Ambiguous Codon Positions", *The Journal of Biological Chemistry*, 260(5):2605-2608 (1985).

Palmenberg, "Proteolytic Processing of Picomoviral Polyprotein", *Annual Review of Microbiology*, 44:603-623 (1990).

Parr et al., "Tumor Selective Transgene Expression in Vivo Mediated by an E2F-Responsive Adenoviral Vector", *Nature Medicine*, 3(10):1145-1149 (1997).

Pearson et al., Improved Tools for Biological Sequence Comparison, *PNAS*, 85:2444-2448 (1988).

Puck et al., "Clonal Growth of Mammalian Cells in Vitro", downloaded from www.jem.org. on May 5, 2005.

Rossolini et al., "Use of Deoxyinosine-Containing Primers vs. Degenerate Primers for Polymerase Chain Reaction Based on Ambiguous Sequence Information", *Molecular and Cellular Probes*, 8:91-98 (1994).

Ryan et al., "Antitumor efficacy and tumor-selective replication with a single intravenous injection of OAS403, an oncolytic adenovirus dependent on two prevalent alterations in human cancer," *Cancer Gene Therapy*, 11:555-569 (2004).

Shay et al., "A Survey of Telomerase Activity in Human Cancer", *European Journal of Cancer*, 33(5):787-791 (1997).

Smith et al., "Comparison of Biosequences", *Advances in Applied Mathematics*, 2:482-489 (1981).

Smith et al., "Transient Immunosuppression Permiots Successful Repetitive Intravenous Administration of an Adenovirus Vector", *Gene Therapy*, 3:496-502 (1996).

Stewart et al., "Telomerase and Human Tumorigenesis", *Cancer Biology*, 10:399-406 (2000).

Strauss et al., "Unrestricted Cell Cycling and Cancer", *Nature Medicine*, 1(12):1245-1246, (1995).

Takahashi et al., "Analysis of Promoter Binding by the E2F and pRB Families in Vivo: Distinct E2F Proteins Mediate Activation and Repression", *Genes and Development*, 14:804-816 (2000).

Weinberg, "The Retinoblastoma Protein and Cell Cycle Control", *Cell*, 81:323-330 (1995).

Wu et al., "Flexibility of the Adenovirus Fiber is Required for Efficient Receptor Interaction", *Journal of Virology*, 77(13):7225-7235 ( 2003).

Zhang et al., "Identification of Human Uroplakin II Promoter and Its Use in the Construction of CG8840, a Urothelium-Specific Adenovirus Variant that Eliminates Established Bladder Tumors in Combination with Docetaxel", *Cancer Research*,62:3743-3750 (2002).

Zwicker, et al., "Cell-Cycle-Regulated Transcription in Mammalian Cells", *Progress in Cell Cycle Research*, 1:91-99 (1995).

SEQUENCE LISTING

<160> NUMBER OF SEQ ID NOS: 14

<210> SEQ ID NO 1
<211> LENGTH: 270
<212> TYPE: DNA
<213> ORGANISM: Human

<400> SEQUENCE: 1
tggtaccatc cggacaaagc ctgcgcgcgc cccgccccgc cattggccgt accgcccgc      60 gccgccgccc catcccgccc ctcgccgccg ggtccggcgc gttaaagcca ataggaaccg    120
ccgccgttgt tcccgtcacg gccggggcag ccaattgtgg cggcgctcgg cggctcgtgg    180
ctctttcgcg gcaaaaagga tttggcgcgt aaaagtggcc gggactttgc aggcagcggc    240
ggccgggggc ggagcgggat cgagccctcg                                     270

<210> SEQ ID NO 2
<211> LENGTH: 239
<212> TYPE: DNA
<213> ORGANISM: Human

<400> SEQUENCE: 2

-continued

| | |
|---|---:|
| cgtggcggag ggactgggga cccgggcacc cgtcctgccc cttcaccttc cagctccgcc | 60 |
| tcctccgcgc ggaccccgcc ccgtcccgac ccctcccggg tccccggccc agccccctcc | 120 |
| gggccctccc agccctccc cttcctttcc gcggccccgc cctctcctcg cggcgcgagt | 180 |
| ttcaggcagc gctgcgtcct gctgcgcacg tgggaagccc tggccccggc caccccgc | 239 |

<210> SEQ ID NO 3
<211> LENGTH: 245
<212> TYPE: DNA
<213> ORGANISM: Human

<400> SEQUENCE: 3

| | |
|---|---:|
| ccccacgtgg cggagggact ggggacccgg gcaccgtcc tgcccttca ccttccagct | 60 |
| ccgcctcctc cgcgcggacc ccgccccgtc ccgaccctc ccgggtcccc ggcccagccc | 120 |
| cctccgggcc ctcccagccc ctccccttcc tttccgcggc ccgccctct cctcgcggcg | 180 |
| cgagtttcag gcagcgctgc gtcctgctgc gcacgtggga gccctggcc ccggccaccc | 240 |
| ccgcg | 245 |

<210> SEQ ID NO 4
<211> LENGTH: 2751
<212> TYPE: DNA
<213> ORGANISM: oncolytic adenovirus

<400> SEQUENCE: 4

| | |
|---|---:|
| catcatcaat aaatatacct tattttggat tgaagccaat atgataatga gggggtggag | 60 |
| tttgtgacgt ggcgcggggc gtgggaacgg ggcgggtgac gtagtagtgt ggcggaagtg | 120 |
| tgatgttgca agtgtggcgg aacacatgta agcgacggat gtggcaaaag tgacgttttt | 180 |
| ggtgtgcgcc ggtgtacaca ggaagtgaca attttcgcgc ggttttaggc ggatgttgta | 240 |
| gtaaatttgg gcgtaaccga gtaagatttg ccattttcg cgggaaaact gaataagagg | 300 |
| aagtgaaatc tgaataattt tgtgttactc atagcgcgta atatttgtct agggccgcgg | 360 |
| ggactttgac cgtttacgtg accgtggta ccatccggac aaagcctgcg cgcgccccgc | 420 |
| ccgccattg gccgtaccgc ccgcgccgc cgccccatcc cgccctcgc cgccgggtcc | 480 |
| ggcgcgttaa agccaatagg aaccgccgcc gttgttccg tcacggccgg ggcagccaat | 540 |
| tgtggcggcg ctcggcggct cgtggctctt tcgcggcaaa aaggatttgg cgcgtaaaag | 600 |
| tggccgggac tttgcaggca gcggcggccg ggggcggagc gggatcgagc cctcgaccgg | 660 |
| tgactgaaaa tgagacatat tatctgccac ggaggtgtta ttaccgaaga aatggccgcc | 720 |
| agtcttttgg accagctgat cgaagaggta ctggctgata atcttccacc tcctagccat | 780 |
| tttgaaccac ctacccttca cgaactgtat gatttagacg tgacggcccc cgaagatccc | 840 |
| aacgaggagg cggtttcgca gatttttccc gactctgtaa tgttggcggt gcaggaaggg | 900 |
| attgacttac тcacтттгтcc gccggcgccc ggttctccgg aggcgcctca cctttcccgg | 960 |
| cagcccgagc agccggagca gagagccttg ggtccggttt ctatgccaaa ccttgtaccg | 1020 |
| gaggtgatcg atcttacctg ccacgaggct ggctttccac ccagtgacga cgaggatgaa | 1080 |
| gagggtgagg agtttgtgtt agattatgtg gagcaccccg ggcacggttg caggтcтттgт | 1140 |
| cattatcacc ggaggaatac ggggacccca gatattatgt gttcgctttg ctatatgagg | 1200 |
| acctgtggca tgtttgtcta cagtaagtga aaattatggg cagtgggtga tagagtggtg | 1260 |
| ggtttggtgt ggtaattttt тттттaaтттт tacagttttg tggtttaaag aaттттгтaт | 1320 |
| tgtgattttt тгтaaaaggтc ctgtgtctga acctgagcct gagcccgagc cagaaccgga | 1380 |

-continued

```
gcctgcaaga cctacccgcc gtcctaaaat ggcgcctgct atcctgagac gcccgacgtc    1440
acctgtgtct agagaatgca atagtagtac ggatagctgt gactccggtc cttctaacac    1500
acctcctgag atacacccgg tggtcccgct gtgccccatt aaaccagttg ccgtgagagt    1560
tggtgggcgt cgccaggctg tggaatgtat cgaggacttg cttaacgagc ctgggcaacc    1620
tttggacttg agctgtaaac gccccaggcc ataaggtgta aacctgtgat gcgtgtgtg    1680 gttaacgcct ttgtttgctg aatggtcgac cggtaccgtg gcggagggac tggggacccg    1740
ggcacccgtc ctgcccttc accttccagc tccgcctcct ccgcgcggac cccgccccgt    1800
cccgacccct cccgggtccc cggcccagcc ccctccgggc cctcccagcc cctcccttc    1860 ctttccgcgg ccccgccctc tcctcgcggc gcgagtttca ggcagcgctg cgtcctgctg    1920
cgcacgtggg aagccctggc cccggccacc cccgcaccgg tcgacgcgct gcggctgctg    1980
ttgctttttt gagttttata aaggataaat ggagcgaaga acccatctg agcgggggt    2040 acctgctgga ttttctggcc atgcatctgt ggagagcggt tgtgagacac aagaatcgcc    2100
tgctactgtt gtcttccgtc cgcccggcga taataccgac ggaggagcag cagcagcagc    2160
aggaggaagc caggcggcgg cggcaggagc agagcccatg gaacccgaga gccggcctgg    2220
accctcggga atgaatgttg tacaggtggc tgaactgtat ccagaactga gacgcatttt    2280
gacaattaca gaggatgggc aggggctaaa ggggtaaag agggagcggg gggcttgtga    2340
ggctacagag gaggctagga atctagcttt tagcttaatg accagacacc gtcctgagtg    2400
tattactttt caacagatca aggataattg cgctaatgag cttgatctgc tggcgcagaa    2460
gtattccata gagcagctga ccacttactg gctgcagcca ggggatgatt ttgaggaggc    2520
tattagggta tatgcaaagg tggcacttag gccagattgc aagtacaaga tcagcaaact    2580
tgtaaatatc aggaattgtt gctacatttc tgggaacggg gccgaggtgg agatagatac    2640
ggaggatagg gtggccttta gatgtagcat gataaatatg tggccggggg tgcttggcat    2700
ggacggggtg gttattatga atgtaaggtt tactggcccc aattttagcg g    2751
```

<210> SEQ ID NO 5
<211> LENGTH: 4020
<212> TYPE: DNA
<213> ORGANISM: oncolytic adenovirus

<400> SEQUENCE: 5

```
catcatcaat aaatatacct tattttggat tgaagccaat atgataatga ggggtggag     60 tttgtgacgt ggcgcggggc gtgggaacgg gcgggtgac gtagtagtgt ggcggaagtg    120
tgatgttgca agtgtggcgg aacacatgta agcgacggat gtggcaaaag tgacgttttt    180
ggtgtgcgcc ggtgtacaca ggaagtgaca attttcgcgc ggttttaggc ggatgttgta    240
gtaaatttgg gcgtaaccga gtaagatttg gccattttcg cgggaaaact gaataagagg    300
aagtgaaatc tgaataattt tgtgttactc atagcgcgta atatttgtct agggccgcgg    360
ggactttgac cgtttacgtg accggtggta ccatccggac aaagcctgcg cgcgccccgc    420
cccgccattg gccgtaccgc cccgcgccgc cgccccatcc cgccctcgc cgccgggtcc    480 ggcgcgttaa agccaatagg aaccgccgcc gttgttcccg tcacggccgg ggcagccaat    540
tgtggcggcg ctcggcggct cgtggctctt tcgcggcaaa aaggatttgg cgcgtaaaag    600
tggccgggac tttgcaggca gcggcggccg gggcgagc gggatcgagc cctcgaccgg    660
tgactgaaaa tgagacatat tatctgccac ggaggtgtta ttaccgaaga aatggccgcc    720
```

```
agtcttttgg accagctgat cgaagaggta ctggctgata atcttccacc tcctagccat    780
tttgaaccac ctaccettca cgaactgtat gatttagacg tgacggcccc cgaagatccc    840
aacgaggagg cggtttcgca gattttccc  gactctgtaa tgttggcggt gcaggaaggg    900
attgacttac tcactttcc  gccggcgccc ggttctccgg aggcgcctca cctttcccgg    960
cagcccgagc agccggagca gagagccttg ggtccggttt ctatgccaaa ccttgtaccg   1020
gaggtgatcg atcttacctg ccacgaggct ggctttccac ccagtgacga cgaggatgaa   1080
gagggtgagg agtttgtgtt agattatgtg gagcaccccg ggcacggttg caggtcttgt   1140
cattatcacc ggaggaatac gggggaccca gatattatgt gttcgctttg ctatatgagg   1200
acctgtggca tgtttgtcta cagtaagtga aaattatggg cagtgggtga tagagtggtg   1260
ggtttggtgt ggtaattttt ttttaatttt tacagttttg tggtttaaag aattttgtat   1320
tgtgattttt ttaaaaggtc ctgtgtctga acctgagcct gagcccgagc cagaaccgga   1380
gcctgcaaga cctacccgcc gtcctaaaat ggcgcctgct atcctgagac gcccgacgtc   1440
acctgtgtct agagaatgca atagtagtac ggatagctgt gactccggtc cttctaacac   1500
acctcctgag atacacccgg tggtcccgct gtgccccatt aaaccagttg ccgtgagagt   1560
tggtgggcgt cgccaggctg tggaatgtat cgaggacttg cttaacgagc ctgggcaacc   1620
tttggacttg agctgtaaac gccccaggcc ataaggtgta aacctgtgat tgcgtgtgtg   1680
gttaacgcct ttgtttgctg aatggtcgac cggtaccgtg gcggagggac tggggacccg   1740
ggcacccgtc ctgcccttc  accttccagc tccgcctcct ccgcgcggac cccgccccgt   1800
cccgaccccct cccgggtccc cggcccagcc ccctccgggc cctcccagcc cctccccttc   1860
cttttccgcgg ccccgccctc tcctcgcggc gcgagtttca ggcagcgctg cgtcctgctg   1920
cgcacgtggg aagccctggc cccggccacc cccgcaccgg tcgacatgga ggcttgggag   1980
tgtttggaag atttttctgc tgtgcgtaac ttgctggaac agagctctaa cagtacctct   2040
tggtttttgga ggtttctgtg gggctcatcc caggcaaagt tagtctgcag aattaaggag   2100
gattacaagt gggaatttga agagcttttg aaatcctgtg gtgagctgtt tgattctttg   2160
aatctgggtc accaggcgct tttccaagag aaggtcatca agactttgga tttttccaca   2220
ccggggcgcg ctgcggctgc tgttgctttt ttgagttta  taaaggataa atggagcgaa   2280
gaaacccatc tgagcggggg gtacctgctg gattttctgg ccatgcatct gtggagagcg   2340
gttgtgagac acaagaatcg cctgctactg ttgtcttccg tccgcccggc gataataccg   2400
acggaggagc agcagcagca gcaggaggaa gccaggcggc ggcggcagga gcagagccca   2460
tggaacccga gagccggcct ggaccctcgg gaatgaatgt tgtacaggtg gctgaactgt   2520
atccagaact gagacgcatt ttgacaatta cagaggatgg gcagggggcta aagggggtaa   2580
agagggagcg ggggggcttgt gaggctacag aggaggctag gaatctagct tttagcttaa   2640
tgaccagaca ccgtcctgag tgtattactt ttcaacagat caaggataat tgcgctaatg   2700
agcttgatct gctggcgcag aagtattcca tagagcagct gaccacttac tggctgcagc   2760
caggggatga ttttgaggag gctattaggg tatatgcaaa ggtggcactt aggccagatt   2820
gcaagtacaa gatcagcaaa cttgtaaata tcaggaattg ttgctacatt tctgggaacg   2880
gggccgaggt ggagatagat acggaggata gggtggcctt tagatgtagc atgataaata   2940
tgtggccggg ggtgcttggc atggacgggg tggttattat gaatgtaagg tttactggcc   3000
ccaattttag cggtacggtt ttcctggcca ataccaacct tatcctacac ggtgtaagct   3060
tctatgggtt taacaatacc tgtgtggaag cctggaccga tgtaagggtt cggggctgtg   3120
```

```
ccttttactg ctgctggaag ggggtggtgt gtcgccccaa aagcagggct tcaattaaga    3180
aatgcctctt tgaaaggtgt accttgggta tcctgtctga gggtaactcc agggtgcgcc    3240
acaatgtggc ctccgactgt ggttgcttca tgctagtgaa aagcgtggct gtgattaagc    3300
ataacatggt atgtggcaac tgcgaggaca gggcctctca gatgctgacc tgctcggacg    3360
gcaactgtca cctgctgaag accattcacg tagccagcca ctctcgcaag gcctggccag    3420
tgtttgagca taacatactg acccgctgtt ccttgcattt gggtaacagg agggggtgt    3480 tcctacctta ccaatgcaat ttgagtcaca ctaagatatt gcttgagccc gagagcatgt    3540
ccaaggtgaa cctgaacggg gtgtttgaca tgaccatgaa gatctggaag gtgctgaggt    3600
acgatgagac ccgcaccagg tgcagaccct gcgagtgtgg cggtaaacat attaggaacc    3660
agcctgtgat gctggatgtg accgaggagc tgaggcccga tcacttggtg ctggcctgca    3720
cccgcgctga gtttggctct agcgatgaag atacagattg aggtactgaa atgtgtgggc    3780
gtggcttaag ggtgggaaag aatatataag gtggggtct tatgtagttt tgtatctgtt    3840
ttgcagcagc cgccgccgcc atgagcacca actcgtttga tggaagcatt gtgagctcat    3900
atttgacaac gcgcatgccc ccatgggccg gggtgcgtca gaatgtgatg ggctccagca    3960
ttgatggtcg ccccgtcctg cccgcaaact ctactacctt gacctacgag accgtgtctg    4020
```

<210> SEQ ID NO 6
<211> LENGTH: 3207
<212> TYPE: DNA
<213> ORGANISM: oncolytic adenovirus

<400> SEQUENCE: 6

```
catcatcaat aaatatacct tattttggat tgaagccaat atgataatga gggggtggag     60
tttgtgacgt ggcgcggggc gtgggaacgg ggcgggtgac gtagtagtgt ggcggaagtg    120
tgatgttgca agtgtggcgg aacacatgta agcgacggat gtggcaaaag tgacgttttt    180
ggtgtgcgcc ggtgtacaca ggaagtgaca attttcgcgc ggttttaggc ggatgttgta    240
gtaaatttgg gcgtaaccga gtaagatttg gccattttcg cgggaaaact gaataagagg    300
aagtgaaatc tgaataattt tgtgttactc atagcgcgta atatttgtct agggccgcgg    360
ggactttgac cgtttacgtg accggtggta ccatccggac aaagcctgcg cgcgccccgc    420
cccgccattg gccgtaccgc cccgcgccgc cgccccatcc cgcccctcgc cgccgggtcc    480
ggcgcgttaa agccaatagg aaccgccgcc gttgttcccg tcacggccgg ggcagccaat    540
tgtggcggcg ctcggcggct cgtggctctt tcgcggcaaa aaggatttgg cgcgtaaaag    600
tggccgggac tttgcaggca gcggcggccg ggggcggagc gggatcgagc cctcgaccgg    660
tgactgaaaa tgagacatat tatctgccac ggaggtgtta ttaccgaaga aatggccgcc    720
agtcttttgg accagctgat cgaagaggta ctggctgata tcttccacc tcctagccat    780 tttgaaccac ctacccttca cgaactgtat gatttagacg tgacggcccc cgaagatccc    840
aacgaggagg cggtttcgca gatttttccc gactctgtaa tgttggcggt gcaggaaggg    900
attgacttac tcacttttcc gccggcgccc ggttctccgg aggcgcctca cctttcccgg    960
cagcccgagc agccggagca gagagccttg gtccggtttc tatgccaaa ccttgtaccg    1020 gaggtgatcg atcttaccctg ccacgaggct ggctttccac ccagtgacga cgaggatgaa    1080
gagggtgagg agtttgtgtt agattatgtg gagcaccccg gcacggttg caggtcttgt    1140 cattatcacc ggaggaatac gggggaccca gatattgtg gttcgctttg ctatatgagg    1200
```

-continued

```
acctgtggca tgtttgtcta cagtaagtga aaattatggg cagtgggtga tagagtggtg    1260
ggtttggtgt ggtaattttt ttttaatttt tacagttttg tggtttaaag aattttgtat    1320
tgtgattttt ttaaaaggtc ctgtgtctga acctgagcct gagcccgagc cagaaccgga    1380
gcctgcaaga cctacccgcc gtcctaaaat ggcgcctgct atcctgagac gcccgacgtc    1440
acctgtgtct agagaatgca atagtagtac ggatagctgt gactccggtc cttctaacac    1500
acctcctgag atacacccgg tggtcccgct gtgcccatt aaaccagttg ccgtgagagt    1560
tggtgggcgt cgccaggctg tggaatgtat cgaggacttg cttaacgagc ctgggcaacc    1620
tttggacttg agctgtaaac gccccaggcc ataaggtgta aacctgtgat tgcgtgtgtg    1680
gttaacgcct ttgtttgctg aatggtcgac taattccggt tattttccac catattgccg    1740
tcttttggca atgtgagggc ccggaaacct ggccctgtct tcttgacgag cattcctagg    1800
ggtctttccc ctctcgccaa aggaatgcaa ggtctgttga atgtcgtgaa ggaagcagtt    1860
cctctggaag cttcttgaag acaaacaacg tctgtagcga ccctttgcag gcagcggaac    1920
cccccacctg gcgacaggtg cctctgcggc caaaagccac gtgtataaga tacacctgca    1980
aaggcggcac aaccccagtg ccacgttgtg agttggatag ttgtggaaag agtcaaatgg    2040
ctctcctcaa gcgtattcaa caaggggctg aaggatgccc agaaggtacc ccattgtatg    2100
ggatctgatc tggggcctcg gtgcacatgc tttacatgtg tttagtcgag gttaaaaaaa    2160
cgtctaggcc ccccgaacca cggggacgtg gttttccttt gaaaaacacg atgtcgacgc    2220
gctgcggctg ctgttgcttt tttgagtttt ataaaggata aatggagcga agaaacccat    2280
ctgagcgggg ggtacctgct ggattttctg gccatgcatc tgtggagagc ggttgtgaga    2340
cacaagaatc gcctgctact gttgtcttcc gtccgcccgg cgataatacc gacggaggag    2400
cagcagcagc agcaggagga agccaggcgg cggcggcagg agcagagccc atggaacccg    2460
agagccggcc tggaccctcg ggaatgaatg ttgtacaggt ggctgaactg tatccagaac    2520
tgagacgcat tttgacaatt acagaggatg ggcagggct aaaggggta aagagggagc    2580 gggggcttg tgaggctaca gaggaggcta ggaatctagc ttttagctta atgaccagac    2640
accgtcctga gtgtattact tttcaacaga tcaaggataa ttgcgctaat gagcttgatc    2700
tgctggcgca aagtattcc atagagcagc tgaccactta ctggctgcag ccaggggatg    2760
attttgagga ggctattagg gtatatgcaa aggtggcact taggccagat tgcaagtaca    2820
agatcagcaa acttgtaaat atcaggaatt gttgctacat ttctgggaac ggggccgagg    2880
tggagataga tacggaggat agggtggcct ttagatgtag catgataaat atgtggccgg    2940
gggtgcttgg catggacggg gtggttatta tgaatgtaag gtttactggc cccaatttta    3000
gcggtacggt tttcctggcc aataccaacc ttatcctaca cggtgtaagc ttctatgggt    3060
ttaacaatac ctgtgtggaa gcctggaccg atgtaagggt tcgggctgt gccttttact    3120 gctgctggaa gggggtggtg tgtcgcccca aaagcagggc ttcaattaag aaatgcctct    3180
ttgaaaggtg taccttgggt atcctgt                                       3207
```

<210> SEQ ID NO 7
<211> LENGTH: 4304
<212> TYPE: DNA
<213> ORGANISM: oncolytic adenovirus

<400> SEQUENCE: 7

```
catcatcaat aaatataccct tattttggat tgaagccaat atgataatga ggggtggag    60 tttgtgacgt ggcgcggggc gtgggaacgg ggcgggtgac gtagtagtgt ggcggaagtg    120
```

-continued

```
tgatgttgca agtgtggcgg aacacatgta agcgacggat gtggcaaaag tgacgttttt    180
ggtgtgcgcc ggtgtacaca ggaagtgaca attttcgcgc ggttttaggc ggatgttgta    240
gtaaatttgg gcgtaaccga gtaagatttg gccattttcg cgggaaaact gaataagagg    300
aagtgaaatc tgaataattt tgtgttactc atagcgcgta atatttgtct agggccgcgg    360
ggactttgac cgtttacgtg accggtaccg tggcggaggg actggggacc cgggcacccg    420
tcctgcccct tcaccttcca gctccgcctc ctccgcgcgg accccgcccc gtcccgaccc    480
ctcccgggtc cccggcccag cccctccgg gccctcccag cccctcccct tcctttccgc     540
ggccccgccc tctcctcgcg gcgcgagttt caggcagcgc tgcgtcctgc tgcgcacgtg    600
ggaagccctg gccccggcca ccccgcacc ggtgactgaa aatgagacat attatctgcc     660
acggaggtgt tattaccgaa gaaatggccg ccagtctttt ggaccagctg atcgaagagg    720
tactggctga taatcttcca cctcctagcc attttgaacc acctacccct cacgaactgt    780
atgatttaga cgtgacggcc cccgaagatc caacgagga ggcggtttcg cagattttc     840
ccgactctgt aatgttggcg gtgcaggaag ggattgactt actcactttt ccgccggcgc    900
ccggttctcc ggagccgcct cacctttccc ggcagcccga gcagccggag cagagagcct    960
tgggtccggt ttctatgcca aaccttgtac cggaggtgat cgatcttacc tgccacgagg   1020
ctggctttcc acccagtgac gacgaggatg aagagggtga ggagtttgtg ttagattatg   1080
tggagcaccc cgggcacggt tgcaggtctt gtcattatca ccggaggaat acggggggacc  1140
cagatattat gtgttcgctt tgctatatga ggacctgtgg catgtttgtc tacagtaagt   1200
gaaaattatg ggcagtgggt gatagagtgg tgggtttggt gtggtaattt ttttttttaat  1260
ttttacagtt ttgtggttta aagaattttg tattgtgatt tttttaaaag gtcctgtgtc   1320
tgaacctgag cctgagcccg agccagaacc ggagcctgca agacctaccc gccgtcctaa   1380
aatgcgcct gctatcctga gacgcccgac atcacctgtg tctagagaat gcaatagtag    1440
tacggatagc tgtgactccg gtccttctaa cacacctcct gagatacacc cggtggtccc   1500
gctgtgccca attaaaccag ttgccgtgag agttggtggg cgtcgccagg ctgtggaatg   1560
tatcgaggac ttgcttaacg agcctgggca acctttggac ttgagctgta acgccccag    1620
gccataaggt gtaaacctgt gattgcgtgt gtggttaacg cctttgtttg ctgaatggtc   1680
gactaattcc ggttattttc caccatattg ccgtcttttg gcaatgtgag ggcccggaaa   1740
cctggccctg tcttcttgac gagcattcct aggggtcttt cccctctcgc caaaggaatg   1800
caaggtctgt tgaatgtcgt gaaggaagca gttcctctgg aagcttcttg aagacaaaca   1860
acgtctgtag cgacccttg caggcagcgg aaccccccac ctggcgacag gtgcctctgc    1920
ggccaaaagc cacgtgtata agatacacct gcaaaggcgg cacaacccca gtgccacgtt   1980
gtgagttgga tagttgtgga aagagtcaaa tggctctcct caagcgtatt caacaagggg   2040
ctgaaggatg cccagaaggt accccattgt atgggatctg atctggggcc tcggtgcaca   2100
tgctttacat gtgtttagtc gaggttaaaa aacgtctagg ccccccgaac cacggggacg   2160
tggttttcct ttgaaaaaca cgatgtcgac atggaggctt gggagtgttt ggaagatttt   2220
tctgctgtgc gtaacttgct ggaacagagc tctaacagta cctcttggtt ttggaggttt   2280
ctgtggggct catcccaggc aaagttagtc tgcagaatta aggaggatta caagtgggaa   2340
tttgaagagc ttttgaaatc ctgtggtgag ctgtttgatt cttgaatct gggtcaccag    2400
gcgcttttcc aagagaaggt catcaagact ttggattttt ccacaccggg gcgcgctgcg   2460
```

-continued

```
gctgctgttg cttttttgag ttttataaag gataaatgga gcgaagaaac ccatctgagc    2520 gggggtacc tgctggattt tctggccatg catctgtgga gagcggttgt gagacacaag     2580
aatcgcctgc tactgttgtc ttccgtccgc ccggcgataa taccgacgga ggagcagcag    2640
cagcagcagg aggaagccag gcggcggcgg caggagcaga gcccatggaa cccgagagcc    2700
ggcctggacc ctcgggaatg aatgttgtac aggtggctga actgtatcca gaactgagac    2760
gcattttgac aattacagag gatgggcagg ggctaaaggg ggtaaagagg gagcgggggg    2820
cttgtgaggc tacagaggag gctaggaatc tagcttttag cttaatgacc agacaccgtc    2880
ctgagtgtat tacttttcaa cagatcaagg ataattgcgc taatgagctt gatctgctgg    2940
cgcagaagta ttccatagag cagctgacca cttactggct gcagccaggg gatgattttg    3000
aggaggctat tagggtatat gcaaaggtgg cacttaggcc agattgcaag tacaagatca    3060
gcaaacttgt aaatatcagg aattgttgct acatttctgg gaacggggcc gaggtggaga    3120
tagatacgga ggatagggtg gccttttagat gtagcatgat aaatatgtgg ccggggtgc    3180 ttggcatgga cggggtggtt attatgaatg taaggtttac tggccccaat tttagcggta    3240
cggttttcct ggccaatacc aaccttatcc tacacggtgt aagcttctat gggtttaaca    3300 ataccctgtgt ggaagcctgg accgatgtaa gggttcgggg ctgtgccttt tactgctgct    3360
ggaagggggg ggtgtgtcgc cccaaaagca gggcttcaat taagaaatgc ctctttgaaa    3420
ggtgtacctt gggtatcctg tctgagggta actccagggt gcgccacaat gtggcctccg    3480
actgtggttg cttcatgcta gtgaaaagcg tggctgtgat taagcataac atggtatgtg    3540
gcaactgcga ggacagggcc tctcagatgc tgacctgctc ggacggcaac tgtcacctgc    3600
tgaagaccat tcacgtagcc agccactctc gcaaggcctg gccagtgttt gagcataaca    3660
tactgacccg ctgttccttg catttgggta acaggagggg ggtgttccta ccttaccaat    3720
gcaatttgag tcacactaag atattgcttg agcccgagag catgtccaag gtgaacctga    3780
acggggtgtt tgacatgacc atgaagatct ggaaggtgct gaggtacgat gagacccgca    3840
ccaggtgcag accctgcgag tgtggcggta acatattag gaaccagcct gtgatgctgg    3900
atgtgaccga ggagctgagg cccgatcact tggtgctggc ctgcacccgc gctgagtttg    3960
gctctagcga tgaagataca gattgaggta ctgaaatgtg tgggcgtggc ttaagggtgg    4020
gaaagaatat ataaggtggg ggtcttatgt agttttgtat ctgttttgca gcagccgccg    4080
ccgccatgag caccaactcg tttgatggaa gcattgtgag ctcatatttg acaacgcgca    4140 tgccccatg ggccggggtg cgtcagaatg tgatgggctc cagcattgat ggtcgccccg    4200
tcctgcccgc aaactctact accttgacct acgagaccgt gtctggaacg ccgttggaga    4260
ctgcagcctc cgccgccgct tcagccgctg cagccaccgc ccgc                    4304
```

<210> SEQ ID NO 8
<211> LENGTH: 34
<212> TYPE: DNA
<213> ORGANISM: synthetic oligonucleotide

<400> SEQUENCE: 8

```
ataccggtgg taccatccgg acaaagcctg cgcg                                 34
```

<210> SEQ ID NO 9
<211> LENGTH: 29
<212> TYPE: DNA
<213> ORGANISM: synthetic oligonucleotide

<400> SEQUENCE: 9

-continued

```
agaccggtcg agggctcgat cccgctccg                                29

<210> SEQ ID NO 10
<211> LENGTH: 35
<212> TYPE: DNA
<213> ORGANISM: synthetic oligonucleotide

<400> SEQUENCE: 10
aagtcgaccg gtaccgtggc ggagggactg gggac                         35

<210> SEQ ID NO 11
<211> LENGTH: 34
<212> TYPE: DNA
<213> ORGANISM: synthetic oligonucleotide

<400> SEQUENCE: 11
aagtcgaccg gtgcgggggt ggccggggcc aggg                          34

<210> SEQ ID NO 12
<211> LENGTH: 261
<212> TYPE: DNA
<213> ORGANISM: adenovirus

<400> SEQUENCE: 12
atggaggctt gggagtgttt ggaagatttt tctgctgtgc gtaacttgct ggaacagagc    60
tctaacagta cctcttggtt ttggaggttt ctgtggggct catcccaggc aaagttagtc   120
tgcagaatta aggaggatta caagtgggaa tttgaagagc ttttgaaatc ctgtggtgag   180
ctgtttgatt ctttgaatct gggtcaccag gcgcttttcc aagagaaggt catcaagact   240
ttggattttt ccacaccggg g                                            261

<210> SEQ ID NO 13
<211> LENGTH: 6
<212> TYPE: DNA
<213> ORGANISM: synthetic oligonucleotide

<400> SEQUENCE: 13 aataaa                                                         6

<210> SEQ ID NO 14
<211> LENGTH: 6
<212> TYPE: RNA
<213> ORGANISM: synthetic oligonucleotide

<400> SEQUENCE: 14 aauaaa                                                         6
```

PAN CANCER ONCOLYTIC VECTORS AND METHODS OF USE THEREOF

This application is a divisional of U.S. patent application Ser. No. 11/074,694, filed Mar. 9, 2005, now U.S. Pat. No. 7,473,418, which application claims the benefit of U.S. provisional application 60/556,549, filed Mar. 25, 2004. These applications are incorporated herein by reference in their entirety.

FIELD OF THE INVENTION

The present invention relates to replication-competent viral vector constructs and their use in the treatment of cancer.

BACKGROUND OF THE INVENTION

Adenoviruses form the basis of some of the most innovative and potentially powerful disease-fighting tools. One such tool is gene therapy, in which an exogenous nucleotide sequence provided to a cell. This approach holds great potential in treating not only cancer, but many other diseases as well, including cystic fibrosis, anemia, hemophilia, diabetes, Hungtington's disease, AIDS, abnormally high serum cholesterol levels, certain immune deficiencies, and many forms of cancer. Gene therapy generally relies upon a delivery vehicle, such as a viral vector in order to provide the exogenous sequence to a cell. Recombinant adenovirus has shown some therapeutic efficacy against these diseases. For reviews, see Kim et al. (1996) *Mol. Med. Today* 12:519-527 and Smith et al. (1996) *Gene Therapy* 3:496-502. Adenoviruses that replicate selectively in target cells are being developed as therapeutic agents for treatment of cancer.

In an alternate approach applicable to cancer treatment, specific attenuated replication-competent viral vectors have been developed for which selective replication in cancer cells preferentially destroys those cells. Various cell-specific replication-competent adenovirus constructs, which preferentially replicate in (and thus destroy) certain cell types, are described in, for example, WO 95/19434, WO 96/17053, WO 98/39464, WO 98/39465, WO 98/39467, WO 98/39466, WO 99/06576, WO 99/25860, WO 00/15820, WO 00/46355, WO 02/067861, WO 02/06862, U.S. Patent application publication US20010053352 and U.S. Pat. Nos. 5,698,443, 5,871, 726, 5,998,205, and 6,432,700. Replication-competent adenovirus vectors have been designed to selectively replicate in tumor cells.

Although replication-competent adenoviruses are able to achieve selective targeting and amplification for the treatment of local and disseminated cancers, there remains a need for improvement in both the adenovirus vectors themselves and methods for their use dependent upon the type of cancer under treatment.

SUMMARY OF THE INVENTION

The present invention provides a recombinant adenoviral vector comprising an adenoviral nucleic acid backbone comprising in sequential order: a left ITR, an adenoviral packaging signal, an E2F responsive promoter or a TERT promoter operatively linked to an E1a coding region, an E2F responsive promoter or a TERT promoter operatively linked to an E1b coding region, and a right ITR.

In another aspect, the transcriptional regulatory element operatively linked to the E1b coding region is an E2F responsive promoter such as the human E2F-1 promoter which comprises SEQ ID NO:1 or a TERT promoter, e.g., a human TERT promoter, such as a human TERT promoter which comprises SEQ ID NO:2 or SEQ ID NO:3.

In another aspect, the recombinant viral vector comprises a mutation in the E1b 19k coding region.

In yet another aspect, the transcriptional element operatively linked to the E1b coding region is an IRES, a TERT promoter, e.g., a human TERT promoter, such as a human TERT promoter which comprises SEQ ID NO:2 or SEQ ID NO:3 or an E2F responsive promoter, such as the human E2F-1 promoter which comprises SEQ ID NO:1.

A recombinant adenoviral vector of the invention may also comprise a mutation or deletion in an E3 coding region, such as E3-6.7, KDa, gp19 KDa, 11.6 KDa (ADP), 10.4 KDa (RIDα), 14.5 KDa (RIDβ), and E3-14.7 Kda or a deletion in the E1b gene such as a deletion in the gene which encodes the E1b 19 kD protein, e.g. the deletion presented as SEQ ID NO:12. The recombinant adenoviral vector may further comprise a transgene.

Exemplary recombinant adenoviral vectors comprise the nucleotide sequences presented as SEQ ID NO: 4 or SEQ ID NO:5, SEQ ID NO:6 or SEQ ID NO:7.

The invention further provides pharmaceutical compositions comprising the adenoviral vectors of the invention and their use in treating a host organism having a neoplastic condition, such as lung, breast, prostate, or colon cancer. In one aspect, the pharmaceutical composition is administered by intratumoral injection.

The invention also provides a method for selective cytolysis of a cancer cell, comprising contacting a cell population with an effective amount of an adenoviral vector of the invention (described above), under conditions wherein the adenoviral vector infects the cells of a cell population resulting in selectively cytolysis of cancer cells within the cell population.

BRIEF DESCRIPTION OF THE DRAWINGS

FIG. 1A depicts the structure of wild-type adenovirus serotype 5.

FIG. 1B depicts the structure of CG5757, which comprises in sequential order a left ITR, an adenoviral packaging signal, a human E2F-1 promoter operatively linked to an E1a coding region, a human telomerase (hTERT) promoter operatively linked to an E1b coding region wherein the E1b coding region comprises a deletion in the E1b19k coding region, and a right ITR.

FIG. 1C depicts the structure of OV947, which comprises in sequential order a left ITR, an adenoviral packaging signal, a human E2F-1 promoter operatively linked to an E1a coding region, an hTERT promoter operatively linked to an E1b coding region, and a right ITR.

FIG. 1D depicts the structure of OV945, which comprises in sequential order a left ITR, an adenoviral packaging signal, a human E2F-1 responsive promoter operatively linked to an E1a coding region, an internal ribosome entry site (IRES) operatively linked to an E1b coding region wherein the E1b coding region comprises a mutation in the E1b19k coding region, and a right ITR.

FIG. 1E depicts the structure of OV948, which comprises in sequential order a left ITR, an adenoviral packaging signal, an hTERT promoter operatively linked to an E1a coding region, a human E2F-1 promoter operatively linked to an E1b coding region, and a right ITR.

FIG. 1F depicts the structure of OV1025, which comprises in sequential order a left ITR, an adenoviral packaging signal, an hTERT promoter operatively linked to an E1a coding region, an internal ribosome entry site (IRES) operatively linked to an E1b coding region, and a right ITR.

FIGS. 3A and 3B show cytotoxicity at 8 days after infection with various MOIs for the cell lines Hep3B and HRE, respectively. FIGS. 3C and 3D show cytotoxicity after infection with an MOI of 1 for different days after infection for the cell lines Hep3B and HRE, respectively.

DETAILED DESCRIPTION OF THE INVENTION

Figure 1:
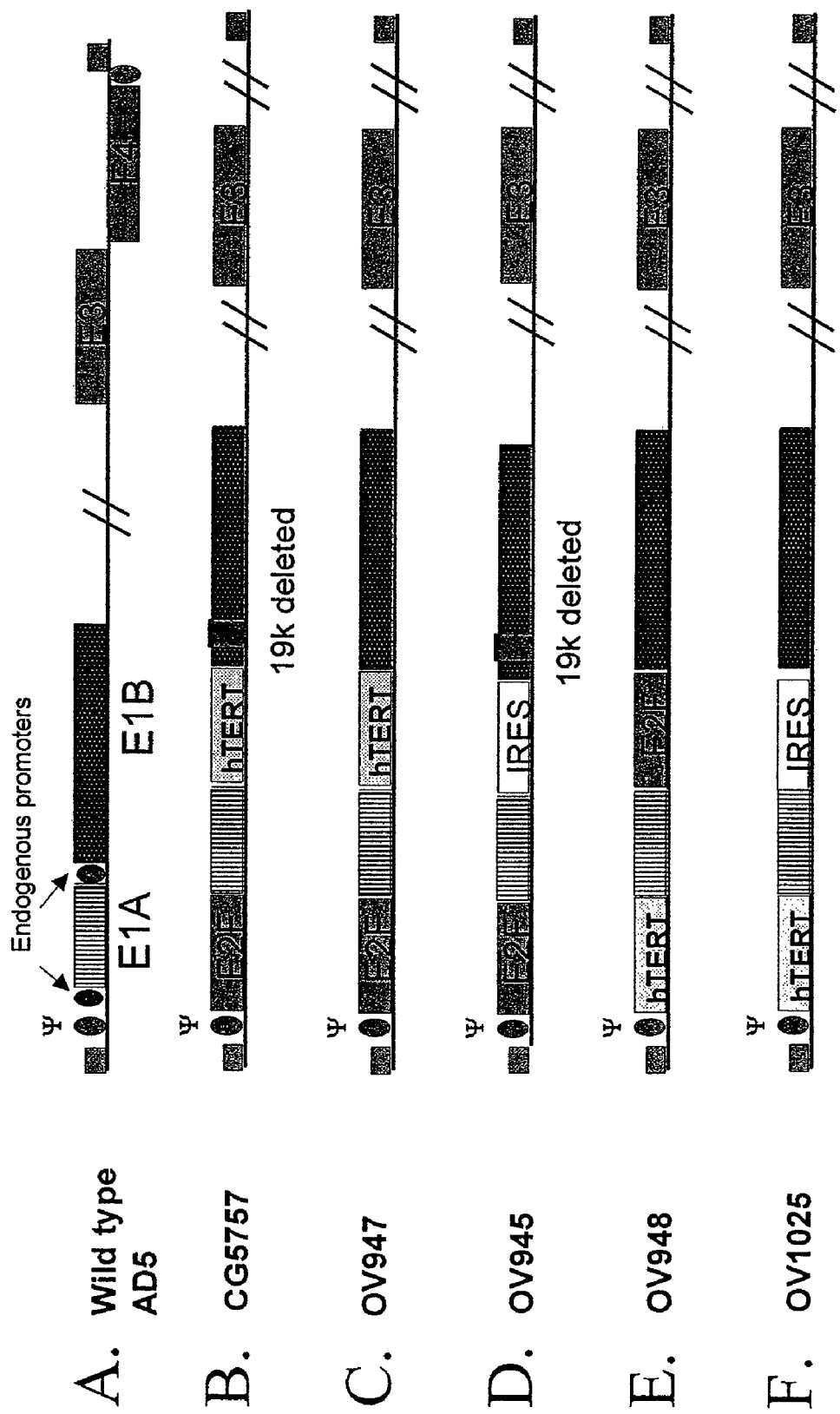
FIGS. 1A-F provide a schematic depiction of the structure of exemplary pan cancer replication-competent viral vector constructs.

Unless otherwise indicated, all terms used herein have the same meaning as they would to one skilled in the art and the practice of the present invention will employ, conventional techniques of microbiology and recombinant DNA technology.

The publications and other materials including all patents, patent applications, publications (including published patent applications), and database accession numbers referred to in this specification are used herein to illuminate the background of the invention and in particular, cases to provide additional details respecting the practice. The publications and other materials including all patents, patent applications, publications (including published patent applications), and database accession numbers referred to in this specification are each individually incorporated herein by reference in its entirety.

In describing the present invention, the following terms are employed and are intended to be defined as indicated below.

The abbreviation "pfu" stands for plaque forming units.

The terms "virus," "viral particle," "vector particle," "viral vector particle," and "virion" are used interchangeably and are to be understood broadly as meaning infectious viral particles that are formed when, e.g., a viral vector of the invention is transduced into an appropriate cell or cell line for the generation of infectious particles. Viral particles according to the invention may be utilized for the purpose of transferring DNA into cells either in vitro or in vivo. For purposes of the present invention, these terms refer to adenoviruses, including recombinant adenoviruses formed when an adenoviral vector of the invention is encapsulated in an adenovirus capsid.

An "adenovirus vector" or "adenoviral vector" (used interchangeably) as referred to herein is a polynucleotide construct, which is replication competent, exhibits preferential replication in cancer cells and contains a tissue-specific transcriptional regulatory sequence linked to an adenoviral gene. In some embodiments, an adenoviral vector of the invention includes a therapeutic gene sequence, e.g., a cytokine gene sequence. Exemplary adenoviral vectors of the invention include, but are not limited to, DNA, DNA encapsulated in an adenovirus coat, adenoviral DNA packaged in another viral or viral-like form (such as herpes simplex, and AAV), adenoviral DNA encapsulated in liposomes, adenoviral DNA complexed with polylysine, adenoviral DNA complexed with synthetic polycationic molecules, conjugated with transferrin, or complexed with compounds such as PEG to immunologically "mask" the antigenicity and/or increase half-life, or conjugated to a nonviral protein. Hence, the terms "adenovirus vector" or "adenoviral vector" as used herein include adenovirus or adenoviral particles.

The terms "adenovirus" and "adenoviral particle" are used to include any and all viruses that may be categorized as an adenovirus, including any adenovirus that infects a human or an animal, including all groups, subgroups, and serotypes. Thus, as used herein, "adenovirus" and "adenovirus particle" refer to the virus itself or derivatives thereof and cover all serotypes and subtypes and both naturally occurring and recombinant forms, except where indicated otherwise (For examples, see Table 1). In one embodiment, such adenoviruses infect human cells. Such adenoviruses may be wild-type or may be modified in various ways known in the art or as disclosed herein. Such modifications include modifications to the adenovirus genome that is packaged in the particle in order to make an infectious virus. Such modifications include deletions known in the art, such as deletions in one or more of the E1a, E1b, E2a, E2b, E3, or E4 coding regions.

The term as used herein "replication-competent" as used herein relative to the adenoviral vectors of the invention means the adenoviral vectors and particles of the invention preferentially replicate in certain types of cells or tissues but to a lesser degree or not at all in other types. In one embodiment of the invention, the adenoviral vector and/or particle selectively replicates in tumor cells and or abnormally proliferating tissue, such as solid tumors and other neoplasms. These include the viruses disclosed in U.S. Pat. Nos. 5,677,178, 5,698,443, 5,871,726, 5,801,029, 5,998,205, and 6,432,700, the disclosures of which are incorporated herein by reference in their entirety. Such viruses may be referred to as "oncolytic viruses" or "oncolytic vectors" and may be considered to be "cytolytic" or "cytopathic" and to effect "selective cytolysis" of target cells.

By "pan-cancer" is meant that the replication-competent adenoviral vectors of the invention selectively replicate in tumor cells and or abnormally proliferating tissue in general and replication is not necessarily limited to a particular type of cancer.

As used herein, the term "viral vector" is used according to its art-recognized meaning. It refers to a nucleic acid vector construct that includes at least one element of viral origin and may be packaged into a viral vector particle. The adenoviral vector and/or particle may be utilized for the purpose of transferring DNA, RNA or other nucleic acid derivatives into cells either in vitro or in vivo. Numerous forms of viral vectors including adenoviral vectors are known in the art.

The terms "vector," "polynucleotide vector," "polynucleotide vector construct," "nucleic acid vector construct," and "vector construct" are used interchangeably herein to mean any nucleic acid construct for gene transfer, as understood by one skilled in the art.

The term "gene essential for replication" refers to a nucleotide sequence whose transcription is required for a viral vector to replicate in a target cell. For example, in an adenoviral vector of the invention, a gene essential for replication may be selected from the group consisting of the E1a, E1b, E2a, E2b, and E4 genes.

As used herein, a "packaging cell" is a cell that is able to package adenoviral genomes or modified genomes to produce viral particles. It can provide a missing gene product or its equivalent. Thus, packaging cells can provide complementing functions for the genes deleted in an adenoviral genome and are able to package the adenoviral genomes into the adenovirus particle. The production of such particles requires that the genome be replicated and that those proteins necessary for assembling an infectious virus are produced. The particles also can require certain proteins necessary for the maturation of the viral particle. Such proteins can be provided by the vector or by the packaging cell.

The term "HeLa-S3" means the human cervical tumor-derived cell line available from American Type Culture Collection (ATCC, Manassas, Va.) and designated as ATCC number CCL-2.2. HeLa-S3 is a clonal derivative of the parent HeLa line (ATCC CCL-2). HeLa-S3 was cloned in 1955 by T. T. Puck et al. (*J. Exp. Med.* 103:273-284 (1956)).

In the context of adenoviral vectors, the term "5'" is used interchangeably with "upstream" and means in the direction of the left inverted terminal repeat (ITR). In the context of adenoviral vectors, the term "3'" is used interchangeably with "downstream" and means in the direction of the right ITR.

The term "nucleic acid" refers to deoxyribonucleotides or ribonucleotides and polymers thereof ("polynucleotides") in either single- or double-stranded form. Unless specifically limited, the term encompasses nucleic acids containing known analogues of natural nucleotides that have similar binding properties as the reference nucleic acid and are metabolized in a manner similar to naturally occurring nucleotides. Unless otherwise indicated, a particular nucleic acid molecule/polynucleotide also implicitly encompasses conservatively modified variants thereof (e.g. degenerate codon substitutions) and complementary sequences and as well as the sequence explicitly indicated. Specifically, degenerate codon substitutions may be achieved by generating sequences in which the third position of one or more selected (or all) codons is substituted with mixed-base and/or deoxyinosine residues (Batzer et al., Nucleic Acid Res. 19: 5081 (1991); Ohtsuka et al., J. Biol. Chem. 260: 2605-2608 (1985); Rossolini et al., Mol. Cell. Probes 8: 91-98 (1994)). Nucleotides are indicated by their bases by the following standard abbreviations: adenine (A), cytosine (C), thymine (T), and guanine (G).

A nucleotide sequence is "operatively linked" when it is placed into a functional relationship with another nucleotide sequence. For example, a promoter or regulatory DNA sequence is said to be "operatively linked" to a DNA sequence that codes for an RNA and/or a protein if the two sequences are operatively linked, or situated such that the promoter or regulatory DNA sequence affects the expression level of the coding or structural DNA sequence. Operatively linked DNA sequences are typically, but not necessarily, contiguous.

The terms "coding sequence" and "coding region" refer to a nucleic acid sequence that is transcribed into RNA such as mRNA, rRNA, tRNA, snRNA, sense RNA or antisense RNA. In one embodiment, the RNA is then translated in a cell to produce a protein.

The term "ORF" means Open Reading Frame.

The term "gene" refers to a defined region that is located within a genome and that, in addition to the aforementioned coding sequence, comprises other, primarily regulatory, nucleic acid sequences responsible for the control of expression, i.e., transcription and translation of the coding portion. A gene may also comprise other 5' and 3' untranslated sequences and termination sequences. Depending on the source of the gene, further elements that may be present are, for example, introns.

The terms "heterologous" and "exogenous" as used herein with reference to nucleic acid molecules such as promoters and gene coding sequences, refer to sequences that originate from a source foreign to a particular virus or host cell or, if from the same source, are modified from their original form. Thus, a heterologous gene in a virus or cell includes a gene that is endogenous to the particular virus or cell but has been modified through, for example, codon optimization. The terms also include non-naturally occurring multiple copies of a naturally occurring nucleic acid sequence. Thus, the terms refer to a nucleic acid segment that is foreign or heterologous to the virus or cell, or homologous to the virus or cell but in a position within the host viral or cellular genome in which it is not ordinarily found.

The terms "complement" and "complementary" refer to two nucleotide sequences that comprise antiparallel nucleotide sequences capable of pairing with one another upon formation of hydrogen bonds between the complementary base residues in the antiparallel nucleotide sequences.

The term "native" refers to a gene that is present in the genome of the wildtype virus or cell.

The term "naturally occurring" or "wildtype" is used to describe an object that can be found in nature as distinct from being artificially produced by man. For example, a protein or nucleotide sequence present in an organism (including a virus), which can be isolated from a source in nature and which has not been intentionally modified by man in the laboratory, is naturally occurring.

The term "recombinant" as used herein with reference to nucleic acid molecules refers to a combination of nucleic acid molecules that are joined together using recombinant DNA technology into a progeny nucleic acid molecule. As used herein with reference to viruses, cells, and organisms, the terms "recombinant," "transformed," and "transgenic" refer to a host virus, cell, or organism into which a heterologous nucleic acid molecule has been introduced. The nucleic acid molecule can be stably integrated into the genome of the host or the nucleic acid molecule can also be present as an extra-chromosomal molecule. Such an extrachromosomal molecule can be auto-replicating. Recombinant viruses, cells, and organisms are understood to encompass not only the end product of a transformation process, but also recombinant progeny thereof. A "non-transformed," "non-transgenic," or "non-recombinant" host refers to a wildtype virus, cell, or organism that does not contain the heterologous nucleic acid molecule.

"Regulatory elements" are nucleotide sequences involved in controlling the expression of a nucleic acid molecule. Regulatory elements include promoters, enhancers, and termination signals. They also typically encompass sequences required for proper translation of the nucleotide sequence.

The term "promoter" refers to an untranslated DNA sequence usually located upstream of the coding region that contains the binding site for RNA polymerase II and initiates transcription of the DNA. The promoter region may also include other elements that act as regulators of gene expression. The term "minimal promoter" refers to a promoter element, particularly a TATA element that is inactive or has greatly reduced promoter activity in the absence of upstream activation elements.

The term "enhancer" within the meaning of the invention may be any genetic element, e.g., a nucleotide sequence that increases transcription of a coding sequence operatively linked to a promoter to an extent greater than the transcription activation effected by the promoter itself when operatively linked to the coding sequence, i.e. it increases transcription from the promoter.

A "termination signal sequence" within the meaning of the invention may be any genetic element that causes RNA polymerase to terminate transcription, such as for example a polyadenylation signal sequence. A polyadenylation signal sequence is a recognition region necessary for endonuclease cleavage of an RNA transcript that is followed by the polyadenylation consensus sequence AATAAA (SEQ ID NO: 13). A polyadenylation signal sequence provides a "polyA site", i.e. a site on a RNA transcript to which adenine residues will be added by post-transcriptional polyadenylation. Polyadenylation signal sequences are useful insulating sequences for transcription units within eukaryotic cells and eukaryotic viruses. Generally, the polyadenylation signal sequence includes a core poly(A) signal that consists of two recognition elements flanking a cleavage-polyadenylation site (e.g., FIG. 1 of WO 02/067861 and WO 02/068627). Typically, an almost invariant AAUAAA (SEQ ID NO: 14) hexamer lies 20 to 50 nucleotides upstream of a more variable element rich in U or GU residues. Cleavage between these two elements is usually on the 3' side of an A residue and, in vitro, is mediated by a large, multicomponent protein complex. The choice of a suitable polyadenylation signal sequence will consider the strength of the polyadenylation signal sequence, as completion of polyadenylation process correlates with poly(A) site strength (Chao et al., Molecular and Cellular Biology, 1999, 19:5588-5600). For example, the strong SV40 late poly(A) site is committed to cleavage more rapidly than the weaker SV40 early poly(A) site. The person skilled in the art will consider to choose a stronger polyadenylation signal sequence if a more substantive reduction of nonspecific transcription is required in a particular vector construct. In principle, any polyadenylation signal sequence may be useful for the purposes of the present invention. However, in preferred embodiments of this invention the termination signal sequence is either the SV40 late polyadenylation signal sequence or the SV40 early polyadenylation signal sequence. In one embodiment of the invention, the termination signal sequence is isolated from its genetic source and inserted into the viral vector at a suitable position upstream of an E2F or TERT promoter.

The term "expression" refers to the transcription and/or translation of an endogenous gene, transgene or coding region in a cell. In the case of an antisense construct, expression may refer to the transcription of the antisense DNA only.

The term "up-regulated" as used herein means that a greater quantity of the RNA for a specific gene can be detected in the target cell as compared to another cell. For example, if a tumor cell that produces more telomerase RNA as compared to a non-tumor cell, the tumor cell has up-regulated expression of telomerase. Expression is considered up regulated when the quantity of specific RNA in a target cell (e.g. tumor cell) is at least 3-fold greater than in another cell (non-tumor cell). In another embodiment, the quantity of specific RNA is at least 5-fold greater. In another embodiment, the quantity of specific RNA is at least 10-fold greater. One skilled in the art knows how to measure RNA levels for a specific RNA sequence (e.g. Northern Assay).

As used herein, an "internal ribosome entry site" or "IRES" refers to an element that promotes direct internal ribosome entry to the initiation codon, such as ATG, of a cistron (a protein encoding region), thereby leading to the cap-independent translation of the gene. Jackson R J, Howell M T, Kaminski A (1990) Trends Biochem Sci 15(12):477-83) and Jackson R J and Kaminski, A. (1995) RNA 1(10):985-1000). The present invention encompasses the use of any IRES element, which is able to promote direct internal ribosome entry to the initiation codon of a cistron. "Under translational control of an IRES" as used herein means that translation is associated with the IRES and proceeds in a cap-independent manner. Examples of "IRES" known in the art include, but are not limited to IRES obtainable from picornavirus (Jackson et al., 1990, Trends Biochem Sci 15(12):477-483); and IRES obtainable from viral or cellular mRNA sources, such as for example, immunoglobulin heavy-chain binding protein (BiP), the vascular endothelial growth factor (VEGF) (Huez et al. (1998) Mol. Cell. Biol. 18(11):6178-6190), the fibroblast growth factor 2, and insulin-like growth factor, the translational initiation factor eIF4G, yeast transcription factors TFIID and HAP4. IRES have also been reported in different viruses such as cardiovirus, rhinovirus, aphthovirus, HCV, Friend murine leukemia virus (FrMLV) and Moloney murine leukemia virus (MoMLV). As used herein, "IRES" encompasses functional variations of IRES sequences as long as the variation is able to promote direct internal ribosome entry to the initiation codon of a cistron. In preferred embodiments, the IRES is mammalian. In other embodiments, the IRES is viral or protozoan. In one illustrative embodiment disclosed herein, the IRES is obtainable from encephelomycarditis virus (ECMV) (commercially available from Novogen, Duke et al. (1992) J. Virol 66(3):1602-1609). In another illustrative embodiment disclosed herein, the IRES is from VEGF. Examples of IRES sequences are described in U.S. Pat. No. 6,692,736.

A "self-processing cleavage site" or "self-processing cleavage sequence" as referred to herein is a nucleotide or amino acid sequence, wherein upon translation, rapid intramolecular (cis) cleavage of a polypeptide comprising the self-processing cleavage site occurs to result in expression of discrete mature protein or polypeptide products. Such a "self-processing cleavage site", may also be referred to as a post-translational or co-translational processing cleavage site, e.g., a 2A site, sequence or domain. A 2A site, sequence or domain demonstrates a translational effect by modifying the activity of the ribosome to promote hydrolysis of an ester linkage, thereby releasing the polypeptide from the translational complex in a manner that allows the synthesis of a discrete downstream translation product to proceed (Donnelly, 2001). Alternatively, a 2A site, sequence or domain demonstrates "auto-proteolysis" or "cleavage" by cleaving its own C-terminus in cis to produce primary cleavage products (Furler; Palmenberg, Ann. Rev. Microbiol. 44:603-623 (1990)).

The term "E2F promoter" as used herein refers to a native E2F promoter and functional fragments, mutations and derivatives thereof. The E2F promoter does not have to be the full-length or wild type promoter. One skilled in the art knows how to derive fragments from an E2F promoter and test them for the desired selectivity. An E2F promoter fragment of the present invention has promoter activity selective for tumor cells, i.e. drives tumor selective expression of an operatively linked coding sequence.

The term "tumor selective promoter activity" as used herein means that the promoter activity of a promoter fragment of the present invention in tumor cells is higher than in non-tumor cell types.

The term "telomerase promoter" or "TERT promoter" as used herein refers to a native TERT promoter and functional fragments, mutations and derivatives thereof. The TERT promoter does not have to be the full-length or wild type promoter. One skilled in the art knows how to derive fragments from a TERT promoter and test them for the desired selectivity. A TERT promoter fragment of the present invention has promoter activity selective for tumor cells, i.e. drives tumor selective expression of an operatively linked coding sequence. In one embodiment, the TERT promoter of the invention is a mammalian TERT promoter. In another embodiment, the mammalian TERT promoter is a human TERT promoter.

In one embodiment, an E2F promoter according to the present invention has a full-length complement that hybridizes to the nucleotide sequence shown in SEQ ID NO:1 under stringent conditions. In another embodiment, the TERT promoter according to the present invention has a full-length complement that hybridizes to the nucleotide sequence shown in SEQ ID NO:2 under stringent conditions. The phrase "hybridizing to" refers to the binding, duplexing, or hybridizing of a molecule to a particular nucleotide sequence under stringent conditions when that nucleotide sequence is present in a complex mixture (e.g., total cellular) DNA or RNA. "Bind(s) substantially" refers to complementary hybridization between a probe nucleic acid and a target nucleic acid and embraces minor mismatches that can be accommodated by reducing the stringency of the hybridization media to achieve the desired detection of the target nucleotide sequence.

"Stringent hybridization conditions" and "stringent wash conditions" in the context of nucleic acid hybridization experiments such as Southern and Northern hybridizations are sequence dependent, and are different under different environmental parameters. Longer sequences hybridize at higher temperatures. An extensive guide to the hybridization of nucleic acids is found in Tijssen (1993) Laboratory Techniques in Biochemistry and Molecular Biology-Hybridization with Nucleic Acid Probes part 1 chapter 2 "Overview of principles of hybridization and the strategy of nucleic acid probe assays" Elsevier, N.Y. Generally, highly stringent hybridization and wash conditions are selected to be about 5° C. to 20° C. (preferably 5° C.) lower than the thermal melting point ($T_m$) for the specific nucleotide sequence at a defined ionic strength and pH. Typically, under highly stringent conditions a probe will hybridize to its target subsequence, but to no other unrelated sequences.

The $T_m$ is the temperature (under defined ionic strength and pH) at which 50% of the target sequence hybridizes to a perfectly matched probe. Very stringent conditions are selected to be equal to the $T_m$ for a particular probe. An example of stringent hybridization conditions for hybridization of complementary nucleic acids that have more than 100 complementary nucleotides on a filter in a Southern or northern blot is 50% formamide with 1 mg of heparin at 42° C., with the hybridization being carried out overnight. An example of high stringency wash conditions is 0.15M NaCl at 72° C. for about 15 minutes. An example of high stringent wash conditions is a 0.2×SSC wash at 65° C. for 15 minutes (see, Sambrook, infra, for a description of SSC buffer). Often, a high stringency wash is preceded by a low stringency wash to remove background probe signal. An example medium stringency wash for a duplex of, e.g., more than 100 nucleotides, is 1×SSC at 45° C. for 15 minutes. An example low stringency wash for a duplex of, e.g., more than 100 nucleotides, is 4-6×SSC at 40° C. for 15 minutes. For short probes (e.g., about 10 to 50 nucleotides), stringent conditions typically involve salt concentrations of less than about 1.0M Na ion, typically about 0.01 to 1.0 M Na ion concentration (or other salts) at pH 7.0 to 8.3, and the temperature is typically at least about 30° C. Stringent conditions can also be achieved with the addition of destabilizing agents such as formamide. In general, a signal to noise ratio of 2× (or higher) than that observed for an unrelated probe in the particular hybridization assay indicates detection of a specific hybridization.

The term "homologous" as used herein with reference to a nucleic acid molecule refers to a nucleotide sequence naturally associated with a host virus or cell.

The terms "identical" or percent "identity" in the context of two or more nucleotide or protein sequences, refer to two or more sequences or subsequences that are the same or have a specified percentage of amino acid residues or nucleotides that are the same, when compared and aligned for maximum correspondence, as measured using one of the sequence comparison algorithms described herein, e.g. the Smith-Waterman algorithm, or by visual inspection.

For sequence comparison, typically one sequence acts as a reference sequence to which test sequences are compared. When using a sequence comparison algorithm, test and reference sequences are input into a computer, subsequence coordinates are designated if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm of Smith &

Waterman, *Adv. Appl. Math.* 2: 482 (1981), by the homology alignment algorithm of Needleman & Wunsch, *J. Mol. Biol.* 48: 443 (1970), by the search for similarity method of Pearson & Lipman, *Proc. Nat'l Acad. Sci. USA* 85: 2444 (1988), by computerized implementations of these algorithms (GAP, BESTFIT, FASTA, and TFASTA in the Wisconsin Genetics Software Package, Genetics Computer Group, 575 Science Dr., Madison, Wis.), by the BLAST algorithm, Altschul et al., *J. Mol. Biol.* 215: 403-410 (1990), with software that is publicly available through the National Center for Biotechnology Information (http://www.ncbi.nlm.nih.gov/), or by visual inspection (see generally, Ausubel et al., infra). For purposes of the present invention, optimal alignment of sequences for comparison is most preferably conducted by the local homology algorithm of Smith & Waterman, Adv. Appl. Math. 2: 482 (1981).

In the context of the present invention, the term "isolated" refers to a nucleic acid molecule, polypeptide, virus, or cell that, by the hand of man, exists apart from its native environment and is therefore not a product of nature. An isolated nucleic acid molecule or polypeptide may exist in a purified form or may exist in a non-native environment such as, for example, a recombinant host cell. An isolated virus or cell may exist in a purified form, such as in a cell culture, or may exist in a non-native environment such as, for example, a recombinant or xenogeneic organism.

A "normal cell status" or "normal physiological state" is the status of a cell which exists in normal physiological conditions and which is non-dividing or divides in a regulated manner, i.e., a cell in a normal physiological state.

An aberrant cell status is defined in relation to a cell of the same type, which is in a non-dividing/regulated dividing state and under normal physiological conditions.

As used herein, the terms "cancer", "cancer cells", "neoplastic cells", "neoplasia", "tumor", and "tumor cells" (used interchangeably) refer to cells that exhibit relatively autonomous growth, so that they exhibit an aberrant growth phenotype or aberrant cell status characterized by a significant loss of control of cell proliferation. Neoplastic cells can be malignant or benign. It follows that cancer cells are considered to have an aberrant cell status.

The term "consists essentially of" or "consisting essentially of" as used herein with reference to a particular nucleotide sequence means that the particular sequence may have additional residues on either the 5' or 3' end or both, wherein the additional residues do not materially affect the basic and novel characteristics of the recited sequence.

The terms "candidate bioactive agent," "drug candidate", "compound" or grammatical equivalents as used herein describes any molecule, e.g., protein, oligopeptide, small organic molecule, polysaccharide, polynucleotide, etc., to be tested for bioactive agents that are capable of directly or indirectly altering the cancer phenotype or the expression of a cancer sequence, including both nucleic acid sequences and protein sequences.

Adenoviral Vectors of the Invention

The present invention provides novel replication-competent adenoviral vectors, examples of which are described in US20010053352, WO 96/17053 and WO 99/25860. In particular, oncolytic adenoviral vectors are disclosed in which expression of an adenoviral gene, which is essential for replication, is controlled by a regulatory region that is selectively transactivated in cancer cells. Thus the adenoviral vectors of the invention are considered to the "pan cancer" vectors. In accordance with the present invention, the pan cancer vectors comprise a cancer selective regulatory region, such as an E2F or TERT promoter described in further detail herein.

The adenoviral vectors of the invention are made by standard techniques known to those skilled in the art. The adenoviral vectors of the invention are transferred into packaging cells in order to generate viral particles by techniques known to those skilled in the art. Packaging cells typically complement any functions deleted from the wild-type adenoviral genome. The production of such particles requires that the vector be replicated and that those proteins necessary for assembling an infectious virus be produced. The packaging cells are cultured under conditions that permit the production of the desired viral vector particle. Viral particles are recovered by standard techniques. The preferred packaging cells are those that have been designed to limit homologous recombination that could lead to wild-type adenoviral particles. Examples of cells that may be used to produce adenoviral particles include the human embryonic kidney cell line 293 (Graham et al., *J. Gen. Virol.* 36:59-72 (1977)), the human embryonic retinoblast cell line PER.C6 (U.S. Pat. Nos. 5,994, 128 and 6,033,908; Fallaux et al., *Hum. Gene Ther.* 9: 1909-1917 (1998)), and the human cervical tumor-derived cell line HeLa-S3 (U.S. patent application 60/463,143; ATCC #CCL-2.2).

The present invention contemplates the use of all adenoviral serotypes to construct the oncolytic adenoviral vectors and adenoviral particles according to the present invention. For example, the adenoviral nucleic acid backbone is derived from adenovirus serotype 2(Ad2), 5 (Ad5) or 35 (Ad35), although other serotype adenoviral vectors can be employed. Adenoviral stocks that can be employed according to the invention include any adenovirus serotype. A large number of adenovirus serotypes are currently available from American Type Culture Collection (ATCC, Manassas, Va.), and the invention includes any other serotype of adenovirus available from any source including those serotypes listed in Table 1. The adenoviruses that can be employed according to the invention may be of human or non-human origin. For instance, an adenovirus can be of subgroup A (e.g., serotypes 12, 18, 31), subgroup B (e.g., serotypes 3, 7, 11, 14, 16, 21, 34, 35), subgroup C (e.g., serotypes 1, 2, 5, 6), subgroup D (e.g., serotypes 8, 9, 10, 13, 15, 17, 19, 20, 22-30, 32, 33, 36-39, 42-47), subgroup E (serotype 4), subgroup F (serotype 40, 41), or any other adenoviral serotype.

TABLE 1

Examples Of Human And Animal Adenoviruses Including The American Type Culture Collection Catalog # For A Representative Virus Of The Respective Classification

| Adenovirus Type | ATCC # |
|---|---|
| Adenovirus Type 21 | ATCC VR-1099 |
| SA18 (Simian adenovirus 18) | ATCC VR-943 |
| SA17 (Simian adenovirus 17) | ATCC VR-942 |
| Adenovirus Type 47 | ATCC VR-1309 |
| Adenovirus Type 44 | ATCC VR-1306 |
| Avian adenovirus Type 4 | ATCC VR-829 |
| Avian adenovirus Type 5 | ATCC VR-830 |
| Avian adenovirus Type 7 | ATCC VR-832 |
| Avian adenovirus Type 8 | ATCC VR-833 |
| Avian adenovirus Type 9 | ATCC VR-834 |
| Avian adenovirus Type 10 | ATCC VR-835 |
| Avian adenovirus Type 2 | ATCC VR-827 |
| Adenovirus Type 45 | ATCC VR-1307 |
| Adenovirus Type 38 | ATCC VR-988 |
| Adenovirus Type 46 | ATCC VR-1308 |
| Simian adenovirus | ATCC VR-541 |
| SA7 (Simian adenovirus 16) | ATCC VR-941 |
| Frog adenovirus (FAV-1) | ATCC VR-896 |

TABLE 1-continued

Examples Of Human And Animal Adenoviruses Including The American Type Culture Collection Catalog # For A Representative Virus Of The Respective Classification

| Adenovirus Type | ATCC # |
|---|---|
| Adenovirus type 48 (candidate) | ATCC VR-1406 |
| Adenovirus Type 42 | ATCC VR-1304 |
| Adenovirus Type 49 (candidate) | ATCC VR-1407 |
| Adenovirus Type 43 | ATCC VR-1305 |
| Avian adenovirus Type 6 | ATCC VR-831 |
| Avian adenovirus Type 3 | |
| Bovine adenovirus Type 3 | ATCC VR-639 |
| Bovine adenovirus Type 6 | ATCC VR-642 |
| Canine adenovirus | ATCC VR-800 |
| Bovine adenovirus Type 5 | ATCC VR-641 |
| Adenovirus Type 36 | ATCC VR-913 |
| Ovine adenovirus type 5 | ATCC VR-1343 |
| Adenovirus Type 29 | ATCC VR-272 |
| Swine adenovirus | ATCC VR-359 |
| Bovine adenovirus Type 4 | ATCC VR-640 |
| Bovine adenovirus Type 8 | ATCC VR-769 |
| Bovine adenovirus Type 7 | ATCC VR-768 |
| Adeno-associated virus Type2 (AAV-2H) | ATCC VR-680 |
| Adenovirus Type 4 | ATCC VR-4 |
| Adeno-associated virus Type3 (AAV-3H) | ATCC VR-681 |
| Peromyscus adenovirus | ATCC VR-528 |
| Adenovirus Type 15 | ATCC VR-661 |
| Adenovirus Type 20 | ATCC VR-662 |
| Chimpanzee adenovirus | ATCC VR-593 |
| Adenovirus Type 31 | ATCC VR-357 |
| Adenovirus Type 25 | ATCC VR-223 |
| Chimpanzee adenovirus | ATCC VR-592 |
| Chimpanzee adenovirus | ATCC VR-591 |
| Adenovirus Type 26 | ATCC VR-224 |
| Adenovirus Type 19 | ATCC VR-254 |
| Adenovirus Type 23 | ATCC VR-258 |
| Adenovirus Type 28 | ATCC VR-226 |
| Adenovirus Type 6 | ATCC VR-6 |
| Adenovirus Type 2 Antiserum: | ATCC VR-1079 |
| Adenovirus Type 6 | ATCC VR-1083 |
| Ovine adenovirus Type 6 | ATCC VR-1340 |
| Adenovirus Type 3 | ATCC VR-847 |
| Adenovirus Type 7 | ATCC VR-7 |
| Adenovirus Type 39 | ATCC VR-932 |
| Adenovirus Type 3 | ATCC VR-3 |
| Bovine adenovirus Type 1 | ATCC VR-313 |
| Adenovirus Type 14 | ATCC VR-15 |
| Adenovirus Type 1 | ATCC VR-1078 |
| Adenovirus Type 21 | ATCC VR-256 |
| Adenovirus Type 18 | ATCC VR-1095 |
| Baboon adenovirus | ATCC VR-275 |
| Adenovirus Type 10 | ATCC VR-11 |
| Adenovirus Type 33 | ATCC VR-626 |
| Adenovirus Type 34 | ATCC VR-716 |
| Adenovirus Type 15 | ATCC VR-16 |
| Adenovirus Type 22 | ATCC VR-257 |
| Adenovirus Type 24 | ATCC VR-259 |
| Adenovirus Type 17 | ATCC VR-1094 |
| Adenovirus Type 4 | ATCC VR-1081 |
| Adenovirus Type 16 | ATCC VR-17 |
| Adenovirus Type 17 | ATCC VR-18 |
| Adenovirus Type 16 | ATCC VR-1093 |
| Bovine adenovirus Type 2 | ATCC VR-314 |
| SV-30 | ATCC VR-203 |
| Adenovirus Type 32 | ATCC VR-625 |
| Adenovirus Type 20 | ATCC VR-255 |
| Adenovirus Type 13 | ATCC VR-14 |
| Adenovirus Type 14 | ATCC VR-1091 |
| Adenovirus Type 18 | ATCC VR-19 |
| SV-39 | ATCC VR-353 |
| Adenovirus Type 11 | ATCC VR-849 |
| Duck adenovirus (Egg drop syndrome) | ATCC VR-921 |
| Adenovirus Type 1 | ATCC VR-1 |
| Chimpanzee adenovirus | ATCC VR-594 |
| Adenovirus Type 15 | ATCC VR-1092 |
| Adenovirus Type 13 | ATCC VR-1090 |
| Adenovirus Type 8 | ATCC VR-1368 |
| SV-31 | ATCC VR-204 |
| Adenovirus Type 9 | ATCC VR-1086 |
| Mouse adenovirus | ATCC VR-550 |
| Adenovirus Type 9 | ATCC VR-10 |
| Adenovirus Type 41 | ATCC VR-930 |
| C1 | ATCC VR-20 |
| Adenovirus Type 40 | ATCC VR-931 |
| Adenovirus Type 37 | ATCC VR-929 |
| Marble spleen disease virus | |
| Adenovirus Type 35 | ATCC VR-718 |
| SV-32 (M3) | ATCC VR-205 |
| Adenovirus Type 28 | ATCC VR-1106 |
| Adenovirus Type 10 | ATCC VR-1087 |
| Adenovirus Type 20 | ATCC VR-1097 |
| Adenovirus Type 21 | ATCC VR-1098 |
| Adenovirus Type 25 | ATCC VR-1103 |
| Adenovirus Type 26 | ATCC VR-1104 |
| Adenovirus Type 31 | ATCC VR-1109 |
| Adenovirus Type 19 | ATCC VR-1096 |
| SV-36 | ATCC VR-208 |
| SV-38 | ATCC VR-355 |
| SV-25 (M8) | ATCC VR-201 |
| SV-15 (M4) | ATCC VR-197 |
| Adenovirus Type 22 | ATCC VR-1100 |
| SV-23 (M2) | ATCC VR-200 |
| Adenovirus Type 11 | ATCC VR-12 |
| Adenovirus Type 24 | ATCC VR-1102 |
| Avian adenovirus Type 1 | |
| SV-11 (M5) | ATCC VR-196 |
| Adenovirus Type 5 | ATCC VR-5 |
| Adenovirus Type 23 | ATCC VR-1101 |
| SV-27 (M9) | ATCC VR-202 |
| Avian adenovirus Type 2 (GAL) | ATCC VR-280 |
| SV-1 (M1) | ATCC VR-195 |
| SV-17 (M6) | ATCC VR-198 |
| Adenovirus Type 29 | ATCC VR-1107 |
| Adenovirus Type 2 | ATCC VR-846 |
| SV-34 | ATCC VR-207 |
| SV-20 (M7) | ATCC VR-199 |
| SV-37 | ATCC VR-209 |
| SV-33 (M10) | ATCC VR-206 |
| Avian adeno-associated virus | ATCC VR-865 |
| Adeno-associated (satellite) virus Type 4 | ATCC VR-646 |
| Adenovirus Type 30 | ATCC VR-273 |
| Adeno-associated (satellite) virus Type1 | ATCC VR-645 |
| Infectious canine hepatitis (Rubarth's disease) | |
| Adenovirus Type 27 | ATCC VR-1105 |
| Adenovirus Type 12 | ATCC VR-863 |
| Adeno-associated virus Type 2 | |
| Adenovirus Type 7a | ATCC VR-848 |

The recombinant adenoviral vectors of this invention are useful as therapeutics for prevention and/or treatment of cancer. The vectors of the invention preferentially replicate in and effect selective cytolysis of tumor cells. In one embodiment, the vectors of the invention, with an E2F promoter operatively linked to a gene essential to replication, preferentially kill Rb-pathway defective tumor cells as compared to cells that are non-defective in the Rb-pathway. In another embodiment, the vectors of the invention, with a TERT promoter operatively linked to a gene essential to replication, preferentially kill tumor cells with up-regulated expression of telomerase as compared to non-tumor cells. In another embodiment, vectors of the invention with both an E2F promoter operatively linked to a gene essential to replication and a TERT promoter operatively linked to a gene essential to replication, preferentially kill tumor cells with both a defect in the Rb-pathway and with up-regulated expression of telomerase. Without wishing to be limited by theoretical considerations, in one embodiment the specific regulation of viral replication by an E2F or TERT promoter is shielded from read-through transcription by an upstream termination signal sequence. In some embodiments, the recombinant viral vectors of the invention further comprise a selective promoter linked to the E4 gene. In other embodiments, the recombinant viral vectors of the invention comprise a 19k deletion in the adenoviral E1b gene. In further embodiments, the recombinant viral vectors of the invention comprise an IRES or self-processing cleavage site (e.g., a 2A) sequence. In still further embodiments the recombinant viral vectors of the invention comprise a heterologous coding sequence or transgene, operatively linked to a native or heterologous promoter. In yet another embodiment, the adenoviral vectors of the invention comprise a targeting ligand. Thus, the combination and the sequential positioning of the genetic elements employed in the vectors of the invention provide for and enhance the vector's selectivity, while at the same time minimizing toxicity and side effects in an animal.

In one embodiment, the recombinant viral vector of the invention comprises a termination signal sequence (as described e.g., in patent publication US20030104624). Insertion of the polyadenylation signal sequences may reduce replication of the oncolytic adenoviral vector in nontarget cells and therefore toxicity. A termination signal sequence may also be placed before (5') any promoter in the vector. In one embodiment, the terminal signal sequence is placed 5' to the E2F promoter, which is operatively linked to the E1a or E1b coding sequences. In another embodiment, the terminal signal sequence is placed 5' to the TERT promoter, which is operatively linked to the E1a or E1b coding sequences.

In an alternative embodiment, the invention further comprises a mutation or deletion in the E1b gene. In one embodiment, the mutation or deletion in the E1b gene is such that the E1b19 kD protein becomes non-functional. This modification of the E1b region may be combined with vectors where all or a part of the E3 region is present. In one embodiment, there is a deletion of E1b (provided as SEQ ID NO:4 or SEQ ID NO:6). In one embodiment the first 261 nucleotides of the E1b open reading frame are deleted. In one embodiment, the nucleotide sequence in SEQ ID NO: 12 is deleted from the vector. In one embodiment, the E1b deletion is the same as the E1b deletion in the viruses CG5757 or OV945.

The oncolytic adenoviral vectors of the invention may optionally comprise a heterologous coding sequence or transgene. For example, the heterologous coding sequence may encode an immunostimulatory protein including, but not limited to, cytokines (GM-CSF, IL1, IL2, IL4, IL5, IFNα, IFNγ, TNFα, IL12, IL18, and flt3), proteins that stimulate interactions with immune cells (B7, CD28, MHC class I, MHC class II, TAPs), tumor-associated antigens (immunogenic sequences from MART-1, gp100 (pmel-17), tyrosinase, tyrosinase-related protein 1, tyrosinase-related protein 2, melanocyte-stimulating hormone receptor, MAGE1, MAGE2, MAGE3, MAGE12, BAGE, GAGE, NY-ESO-1, β-catenin, MUM-1, CDK4, caspase 8, KIA 0205, HLA-A2R1701, α-fetoprotein, telomerase catalytic protein, G-250, MUC-1, carcinoembryonic protein, p53, Her2/neu, triosephosphate isomerase, CDC-27, LDLR-FUT, telomerase reverse transcriptase, and PSMA), antibodies that block inhibitory signals (CTLA4 blockade), chemokines (MIP1α, MIP3α, CCR7 ligand, and calreticulin), and other proteins.

In another embodiment, the heterologous coding sequence codes for an anti-angiogenic protein. Anti-angiogenic proteins include, but are not limited to, METH-1, METH-2, TrpRS fragments, proliferin-related protein, prolactin fragment, PEDF, vasostatin, various fragments of extracellular matrix proteins and growth factor/cytokine inhibitors. Various fragments of extracellular matrix proteins include, but are not limited to, angiostatin, endostatin, kininostatin, fibrinogen-E fragment, thrombospondin, tumstatin, canstatin, and restin.

In another embodiment, the heterologous coding sequence codes for a growth factor/cytokine inhibitor. Growth factor/cytokine inhibitors include, but are not limited to, VEGF/VEGFR antagonist, sFlt-1, sFlk, sNRP1, angiopoietin/tie antagonist, sTie-2, chemokines (IP-10, PF4, Gro-beta, FGF/FGFR antagonist (sFGFR), Ephrin/Eph antagonist (sEphB4 and sephrinB2), inhibitors of factors including IFN-gamma (Mig), IFNα, PDGF, TGFβ and IGF-1; and the like.

In another embodiment, the heterologous coding sequence codes for a suicide gene. A "suicide gene" encodes for a protein which itself can lead to cell death, as with expression of diphtheria toxin A, or the expression of the protein can render cells selectively sensitive to certain drugs, e.g., expression of the Herpes simplex thymidine kinase gene. (HSV-TK) renders cells sensitive to antiviral compounds, such as acyclovir, gancyclovir and FIAU (1-(2-deoxy-2-fluoro-.beta.-D-arabinofuranosil)-5-io-douracil). Other suicide genes include, but are not limited to, genes that encode for carboxypeptidase G2 (CPG2), carboxylesterase (CA), cytosine deaminase (CD), cytochrome P450 (cyt450), deoxycytidine kinase (dCK), nitroreductase (NR), purine nucleoside phosphorylase (PNP), thymidine phosphorylase (TP), varicella zoster virus thymidine kinase (VZV-TK), and xanthine-guanine phosphoribosyl transferase (XGPRT). The heterologous gene can exert its effect at the level of RNA, for instance, by encoding an antisense message or ribozyme, a protein that affects splicing or 3' processing (e.g., polyadenylation), or a protein that affects the level of expression of another gene within the cell, e.g. by mediating an altered rate of mRNA accumulation, an alteration of mRNA transport, and/or a change in post-transcriptional regulation. The addition of a heterologous gene to the virus could result in a virus with an additional antitumor mechanism of action.

In another embodiment, the adenoviral vectors of the invention further comprise a targeting ligand included in a capsid protein of the particle. In one embodiment, the capsid protein is a fiber protein and the ligand is in the HI loop of the fiber protein. In another embodiment, the capsid protein is a fiber protein or pIx. In yet another embodiment, the targeting ligand is in the HI loop of the fiber protein. In a further embodiment, the ligand is added to the carboxyl end of the adenovirus fiber protein. In an additional embodiment, the virus is targeted by replacing the fiber knob with a fiber knob from another adenovirus serotype. For examples of targeted adenoviruses, see for example, WO 00/67576, WO 99/39734, U.S. Pat. No. 6,683,170, U.S. Pat. No. 6,555,368, U.S. Pat. No. 5,922,315, U.S. Pat. No. 5,543,328 and U.S. Pat. No. 5,846,782, The adenoviral vector particle may also include other mutations to the fiber protein. Examples of these mutations include, but are not limited to those described in U.S. application Ser. No. 10/403,337, WO 98/07877, WO 01/92299, and U.S. Pat. Nos. 5,962,311, 6,153,435, 6,455,314 and Wu et al. (J. Virol. 2003 Jul. 1; 77(13):7225-7235). These include, but are not limited to mutations that decrease binding of the viral vector particle to a particular cell type or more than one cell type, enhance the binding of the viral vector particle to a particular cell type or more than one cell type and/or reduce the immune response to the adenoviral vector particle in an animal. In addition, the adenoviral vectors of the present invention may also contain mutations to other viral capsid proteins. Examples of these mutations include, but are not limited to those described in U.S. Pat. Nos. 5,731,190, 6,127,525, and 5,922,315. Other mutated adenoviruses are described in U.S. Pat. Nos. 6,057,155, 5,543,328 and 5,756,086.

Accordingly, in another aspect there is provided a method of selective cytolysis, i.e., killing a neoplastic cell in a cell population that comprises contacting an effective amount of the viral vectors and/or viral particles of the invention with said cell population under conditions where the viral vectors and/or particles can infect the neoplastic cells in the cell population, selectively replicate in and kill the neoplastic cells. The cell population may be in vivo, in vitro or in an ex vivo setting.

The invention further comprises adenoviral vector particles, in which a targeting ligand is included in a capsid protein of the particle. In a further embodiment, the capsid protein is a fiber protein and the ligand is in the HI loop of the fiber protein.

The adenoviral vectors of the invention are made by standard techniques known to those skilled in the art. The vectors are transferred into packaging cells by techniques known to those skilled in the art. Packaging cells provide complementing functions to the adenovirus genomes that are to be packaged into the adenovirus particle. The production of such particles requires that the vector be replicated and that those proteins necessary for assembling an infectious virus be produced. The packaging cells are cultured under conditions that permit the production of the desired viral vector particle. The particles are recovered by standard techniques. Examples of packaging cells include, but are not limited to, packaging cells that have been designed to limit homologous recombination that could lead to wild-type adenoviral particles, for example, cells disclosed in U.S. Pat. Nos. 5,994,128 (Fallaux, et al.) and 6,033,908 (Bout, et al). Also, viral vector particles of the invention may be, for example, produced in PerC6 or Hela-S3 cells (e.g. see U.S. patent application 60/463,143).

E2F Promoters

Without being bound by theory, the selectivity of E2F-responsive promoters (hereinafter sometimes referred to as E2F promoters) is reported to be based on the depression of the E2F promoter/transactivator in Rb-pathway defective tumor cells. In quiescent cells, E2F binds to the tumor suppressor protein pRB in ternary complexes. In its complexed form, E2F functions to repress transcriptional activity from promoters with E2F binding sites, including the E2F-1 promoter itself (Zwicker J, and Muller R., Prog. Cell Cycle Res 1995; 1:91-99). The E2F-1 promoter is transcriptionally inactive in resting cells. In normal cycling cells, pRB-E2F complexes are dissociated in a regulated fashion, allowing for controlled depression of E2F and subsequent cell cycling (Dyson, N., Genes and Development 1998; 12:2245-2262).

In the majority of tumor types, the Rb cell cycle regulatory pathway is disrupted, suggesting that Rb-pathway deregulation is obligatory for tumorigenesis (Strauss M, Lukass J and Bartek J., Nat Med 1995; 12:1245-1246). One consequence of these mutations is the disruption of E2F-pRB binding and an increase in free E2F in tumor cells. Rb itself is mutated in some tumor types, and in other tumor types factors upstream of Rb are deregulated (Weinberg, R A. Cell 1995; 81:323-330). One effect of these Rb-pathway changes in tumors is the loss of pRB binding to E2F, and an apparent increase in free E2F in tumor cells. The abundance of free E2F in turn results in high-level expression of E2F responsive genes in tumor cells, including the E2F-1 gene. Accordingly, the term "Rb-pathway defective cells" may be functionally defined as cells which display an abundance of "free" E2F, as measured by gel mobility shift assay or by chromatin immunoprecipitation (Takahashi Y et al., Genes Dev. 2000 Apr. 1; 14(7):804-16). The E2F-1 promoter has been shown to up-regulate the expression of marker genes in an adenovirus vector in a rodent tumor model but not normal proliferating cells in vivo (Parr M J et al., Nature Med 1997; October; 3(10): 1145-1149).

An E2F-responsive promoter has at least one E2F binding site. In one embodiment, the E2F-responsive promoter is a mammalian E2F promoter. In another embodiment, it is a human E2F promoter. For example, the E2F promoter may be the human E2F-1 promoter. Further, the human E2F-1 promoter may be, for example, a E2F-1 promoter having the sequence as described in SEQ ID NO:1. A number of examples of E2F promoters are known in the art (e.g. Parr et al. Nature Medicine 1997:3 (10) 1145-1149, WO 02/067861, US20010053352 and WO 98/13508). E2F responsive promoters typically share common features such as Sp I and/or ATT7 sites in proximity to their E2F site(s), which are frequently located near the transcription start site, and lack of a recognizable TATA box. E2F-responsive promoters include E2F promoters such as the E2F-1 promoter, dihydrofolate reductase (DHFR) promoter, DNA polymerase A (DPA) promoter, c-myc promoter and the B-myb promoter. The E2F-1 promoter contains four E2F sites that act as transcriptional repressor elements in serum-starved cells. In one embodiment, an E2F-responsive promoter has at least two E2F sites. In another embodiment, an E2F promoter is operatively linked to the adenovirus E1a region. In a further embodiment, an E2F promoter is operatively linked to the adenovirus E1b region. In yet a further embodiment, an E2F promoter is operatively linked to the adenovirus E4 region.

In one embodiment of the invention, the recombinant viral vectors of the present invention selectively replicate in and lyse Rb-pathway defective cells. In one embodiment, the E2F promoter of the invention is a mammalian E2F promoter. In another embodiment, the mammalian E2F promoter is a human E2F promoter, for example a human E2F promoter which comprises or consists essentially of SEQ ID NO:1. Embodiments of the invention include adenoviral vectors comprising an E2F promoter wherein the E2F promoter comprises a nucleotide sequence selected from the group consisting of: (a) the nucleotide sequence shown in SEQ ID NO:1; (b) a fragment of the nucleotide sequence shown in SEQ ID NO:1, wherein the fragment has tumor selective promoter activity; (c) a nucleotide sequence having at least 90, 91, 92, 93, 94, 95, 96, 97, 98, 99% or more % identity over its entire length to the nucleotide sequence shown in SEQ ID NO:1, wherein the nucleotide sequence has tumor selective promoter activity; and (d) a nucleotide sequence having a full-length complement that hybridizes under stringent conditions to the nucleotide sequence shown in SEQ ID NO:1, wherein the nucleotide sequence has tumor selective promoter activity. In another embodiment of the invention, the E2F promoter comprises nucleotides 7 to 270 of SEQ ID NO:1. In another embodiment of the invention, the E2F promoter comprises nucleotides 7 to 270 of SEQ ID NO:1, wherein nucleotide 75 of SEQ ID NO:1 is a T instead of a C.

In other embodiments, a E2F promoter according to the present invention has at least 80, 85, 87, 89, 90, 91, 92, 93, 94, 95, 96, 97, 98, 99% or more sequence identity to the nucleotide sequence shown in SEQ ID NO:1, when compared and aligned for maximum correspondence, as measured using one of the following sequence comparison algorithms or by visual inspection. In one embodiment, the given % sequence identity exists over a region of the sequences that is at least about 50 nucleotides in length. In another embodiment, the given % sequence identity exists over a region of at least about 100 nucleotides in length. In another embodiment, the given % sequence identity exists over a region of at least about 200 nucleotides in length. In another embodiment, the given % sequence identity exists over the entire length of the sequence.

The E2F-responsive promoter does not have to be the full-length or wild type promoter, but should have a tumor-selectivity of at least 3-fold, at least 5-fold, at least 10-fold, at least 20-fold, at least 30-fold, at least 50-fold, at least 100-fold or even at least 300-fold. Tumor-selectivity can be determined by a number of assays using known techniques, such as the techniques employed in WO 02/067861, Example 4, for example RT-PCR or a comparison of replication in selected cell types. The tumor-selectivity of the adenoviral vectors can also be quantified by E1A RNA levels, as further described in WO 02/067861, Example 4, and the E1A RNA levels obtained in H460 (ATCC, Cat. # HTB-177) cells can be compared to those in PERC (Clonetics Cat. #CC2555) cells in order to determine tumor-selectivity for the purposes of this invention. The relevant conditions of the experiment may vary, but typically follow those described in WO 02/067861.

Telomerase (TERT) Promoters

Without being bound by theory, the understanding of selective TERT expression in cancer is based on the current knowledge that TERT is the rate-limiting catalytic subunit of telomerase, a multicomponent ribonucleoprotein enzyme that has also been shown to be active in ~85% of human cancers but not normal somatic cells (Kilian A et al. Hum Mol. Genet. 1997 November; 6(12):2011-9; Kim N W et al. Science. 1994 Dec. 23; 266(5193):2011-5; Shay J W et al. European Journal of Cancer 1997; 5, 787-791; Stewart S A et al. Semin Cancer Biol. 2000 December; 10(6):399-406). Cancer cells appear to require immortalization for tumorigenesis and telomerase activity is almost always necessary for immortalization (Kim N W et al. Science. 1994 Dec. 23; 266(5193):2011-5; Kiyono T et al. Nature 1998; 396:84). Thus, the majority of tumor cells have a disregulated telomerase pathway. Such tumor cells are specifically targeted by viruses of the invention utilizing a TERT promoter operatively linked to a gene and/or coding region essential for replication (e.g. E1a, E1b or E4).

The term TERT promoter as used herein refers to a full-length TERT promoter and functional fragments, mutations and derivatives thereof. The TERT promoter does not have to be a full-length or wild type promoter. One skilled in the art knows how to derive fragments from a TERT promoter and test them for the desired specificity. In one embodiment, a TERT promoter of the invention is a mammalian TERT promoter. In a further embodiment the mammalian TERT promoter, is a human TERT promoter (hTERT). In one embodiment of the invention, the TERT promoter comprises or consists essentially of SEQ ID NO:2, which is a 239 bp fragment of the hTERT promoter. In another embodiment of the invention, the TERT promoter comprises or consists essentially of SEQ ID NO:3, which is a 245 bp fragment of the hTERT promoter. In one embodiment, a TERT promoter is operatively linked to the adenovirus E1a region. In another embodiment, the TERT promoter is operatively linked to the adenovirus E1b region. In yet a further embodiment, the TERT promoter is operatively linked to the adenovirus E4 region.

Embodiments of the invention include adenoviral vectors comprising a TERT promoter wherein the TERT promoter comprises a nucleotide sequence selected from the group consisting of: (a) the nucleotide sequence shown in SEQ ID NO:2; (b) a fragment of the sequence shown in SEQ ID NO:2, wherein the fragment has tumor selective promoter activity; (c) a nucleotide sequence having at least 90% identity over its entire length to the sequence shown in SEQ ID NO:2, wherein the nucleotide sequence has tumor selective promoter activity; and (f) a nucleotide sequence having a full-length complement that hybridizes under stringent conditions to the sequence shown in SEQ ID NO:2, wherein the nucleotide sequence has tumor selective promoter activity. Other examples of TERT promoters are known to those skilled in the art (e.g. WO 98/14593).

In other embodiments, an TERT promoter according to the present invention has at least In other embodiments, a E2F promoter according to the present invention has at least 80, 85, 87, 89, 90, 91, 92, 93, 94, 95, 96, 97, 98, 99% or more sequence identity to the sequence shown in SEQ ID NO:2 or SEQ ID NO; 3, when compared and aligned for maximum correspondence, as measured using one of the following sequence comparison algorithms or by visual inspection. In one embodiment, the given % sequence identity exists over a region of the sequences that is at least about 50 nucleotides in length. In another embodiment, the given % sequence identity exists over a region of at least about 100 nucleotides. In another embodiment, the given % sequence identity exists over a region of at least about 200 nucleotides. In another embodiment, the given % sequence identity exists over the entire length of the sequence.

Compositions and Methods for Practicing the Invention

In a further aspect of the invention, a pharmaceutical composition comprising the recombinant viral vectors and/or particles of the invention and a pharmaceutically acceptable carrier is provided. Such compositions, which can comprise an effective amount of adenoviral vector of the invention in a pharmaceutically acceptable carrier, are suitable for local or systemic administration to individuals in unit dosage forms, sterile parenteral solutions or suspensions, sterile non-parenteral solutions or oral solutions or suspensions, oil in water or water in oil emulsions and the like. Formulations for parenteral and non-parenteral drug delivery are known in the art. Compositions also include lyophilized and/or reconstituted forms of the adenoviral vectors and particles of the invention. Acceptable pharmaceutical carriers are, for example, saline solution, protamine sulfate (Elkins-Sinn, Inc., Cherry Hill, N.J.), water, aqueous buffers, such as phosphate buffers and Tris buffers, or Polybrene (Sigma Chemical, St. Louis Mo.) and phosphate-buffered saline and sucrose. The selection of a suitable pharmaceutical carrier is deemed to be apparent to those skilled in the art from the teachings contained herein. These solutions are sterile and generally free of particulate matter other than the desired adenoviral virions. The compositions may contain pharmaceutically acceptable auxiliary substances as required to approximate physiological conditions such as pH adjusting and buffering agents, toxicity adjusting agents and the like, for example sodium acetate, sodium chloride, potassium chloride, calcium chloride, sodium lactate, etc. Excipients that enhance infection of cells by adenovirus and/or anaesthetics, e.g., lidocaine, may be included.

The viral vectors are administered to a host in an amount that is effective to inhibit, prevent, or destroy the growth of the tumor cells through replication of the viral vectors in the tumor cells. Such administration may be by systemic administration as herein described, or by direct injection of the vectors into a tumor. In one approach, the vectors are administered systemically in an amount of at least $5 \times 10^9$ viral particles per kilogram body weight and in general, such an amount does not exceed $1 \times 10^{13}$ viral particles per kilogram body weight. In another approach, the vectors are administered intratumorally in an amount of at least $2 \times 10^{10}$ viral particles and in general such an amount does not exceed $1 \times 10^{13}$ viral particles per kilogram body weight. In yet another approach, the vectors are instilled into the bladder of the subject. In such cases, the transduction may be pre-treated with a transduction enhancer such as described in U.S. Ser. No. 10/327,869. The exact dosage to be administered is dependent upon a variety of factors including the age, weight, and sex of the patient, and the size and severity of the tumor being treated. The vectors may be administered one or more times. Single or multiple administrations of the compositions can be carried out with dose levels and pattern being selected by the treating physician. If necessary, the immune response may be diminished by employing a variety of immunosuppressants, or removal or preexisting antibodies, so as to permit repetitive administration and/or enhance replication by reducing the immune response to the viruses. Administration of the adenoviral vectors of the present invention may be combined with other antineoplastic protocols, numerous examples of which are known in the art. Such antineoplastic protocols will vary dependent upon the type of cancer under treatment.

Delivery can be achieved in a variety of ways, employing liposomes, direct injection, systemic injection, catheters, topical applications, inhalation, etc.

It follow that the invention provides a method of treating a subject having a neoplastic condition, comprising administering a therapeutically effective amount of an adenoviral vector of the invention to the subject, typically a patient with cancer. While the mechanism is not part of the invention, the viral vectors described herein are believed to distribute selective to tumor cells and essentially throughout a tumor mass due to the capacity for selective replication in the tumor tissue.

All neoplastic conditions are potentially amenable to treatment with the methods of the invention. Tumor types include, but are not limited to hematopoietic, pancreatic, neurologic, hepatic, gastrointestinal tract, endocrine, biliary tract, sinopulmonary, head and neck, soft tissue sarcoma and carcinoma, dermatologic, reproductive tract, respiratory, and the like. In one embodiment, the tumors for treatment are those with a high mitotic index relative to normal tissue. In another embodiment, the tumors are solid tumors.

In one embodiment the subject is a human patient. For human patients, if a heterologous coding sequence is included in the vector, the heterologous coding sequence may be of human origin although genes of closely related species that exhibit high homology and biologically identical or equivalent function in humans may be used if the product of the heterologous coding sequence does not produce/cause an adverse immune reaction in the recipient. In one embodiment, the heterologous coding sequence codes for a therapeutic protein or therapeutic RNA. A therapeutic active amount of a nucleic acid sequence or a therapeutic gene is an amount effective at dosages and for a period of time necessary to achieve the desired result. This amount may vary according to various factors including but not limited to sex, age, weight of a subject, and the like.

The invention also provides for screening candidate drugs to identify agents useful for modulating the expression of E2F and/or TERT, and hence useful for treating cancer. Appropriate host cells are those in which the regulatory region of E2F and/or TERT is capable of functioning. In one embodiment, the regulatory region of E2F and/or TERT is used to make a variety of expression vectors to express a marker that can then be used in screening assays. In one embodiment, the marker is E1a, E1b, viral replication or combinations thereof, all of which can be measured using techniques well known to those skilled in the art. The expression vectors may be either self-replicating extrachromosomal vectors or vectors that integrate into a host genome. Generally, these expression vectors include a transcriptional and translational regulatory nucleic acid sequence of E2F and/or TERT operatively linked to a nucleic acid encoding a marker. The marker may be any protein that can be readily detected. It may be a detected on the basis of light emission, such as luciferase or FITC, color, such as β-galactosidase, enzyme activity, such as alkaline phosphatase or antibody reaction, such as a protein for which an antibody exists. In addition, the marker system may be a viral vector or particle of the present invention.

In one embodiment, a viral vector of the invention is used to assess the anti-cancer efficacy of a candidate therapeutic agent. According to this embodiment, an effective amount of the viral vectors is contacted with a cell population under conditions where the viral vectors can infect the neoplastic cells in the cell population, selectively replicate in, and kill the neoplastic cells. The $LD_{50}$ of the viral vector in the presence and absence of the candidate agent is compared to identify the candidate agents that modulate the expression of the E2F and/or TERT gene or enhance the efficacy of the viral vector in terms of selective cytolysis of cancer cells. If the level of expression is different as compared to similar viral vector controls lacking the E2F and/or TERT promoter, the candidate agent is capable of modulating the expression of E2F and/or TERT and is a candidate for treating cancers and for further development of active agents on the basis of the candidate agent so identified.

In a second embodiment, the candidate agent is added to host cells containing the expression vector and the level of expression of the marker is compared with a control. If the level of expression is different, the candidate agent is capable of modulating the expression of E2F or TERT and is a candidate for treating cancers involving these genes and for further development of active agents on the basis of the candidate agent so identified.

Active agents so identified may also be used in combination treatments, for example with oncolytic adenoviruses of the invention.

In preferred embodiments, the bioactive agents modulate the expression profiles, or expression profile nucleic acids or proteins provided herein. In a particularly preferred embodiment, the candidate agent suppresses a cancer phenotype, for example relative to a normal tissue phenotype.

Candidate agents encompass numerous chemical classes, though typically they are organic molecules, e.g. small organic compounds having a molecular weight of more than 100 and less than about 2,500 daltons. Preferred small molecules are less than 2000, or less than 1500 or less than 1000 or less than 500 daltons. Candidate agents comprise functional groups necessary for structural interaction with proteins, particularly hydrogen bonding, and typically include at least an amine, carbonyl, hydroxyl or carboxyl group, e.g. at least two of the functional chemical groups. The candidate agents often comprise cyclical carbon or heterocyclic structures and/or aromatic or polyaromatic structures substituted with one or more of the above functional groups. Candidate agents are also found among biomolecules including peptides, saccharides, fatty acids, steroids, purines, pyrimidines, derivatives, structural analogs or combinations thereof. Particularly preferred are peptides.

Candidate agents are obtained from a wide variety of sources including libraries of synthetic or natural compounds. For example, numerous means are available for random and directed synthesis of a wide variety of organic compounds and biomolecules, including expression of randomized oligonucleotides. Alternatively, libraries of natural compounds in the form of bacterial, fungal, plant and animal extracts are available or readily produced. Additionally, natural or synthetically produced libraries and compounds are readily modified through conventional chemical, physical and biochemical means. Known pharmacological agents may be subjected to directed or random chemical modifications, such as acylation, alkylation, esterification, amidification to produce structural analogs.

The practice of the present invention employs, unless otherwise indicated, conventional techniques of chemistry, molecular biology, microbiology, recombinant DNA, genetics, immunology, cell biology, cell culture and transgenic biology, which are within the skill of the art. See, e.g., Maniatis et al., 1982, *Molecular Cloning* (Cold Spring Harbor Laboratory Press, Cold Spring Harbor, N.Y.); Sambrook et al., 1989, *Molecular Cloning*, 2nd Ed. (Cold Spring Harbor Laboratory Press, Cold Spring Harbor, N.Y.); Sambrook and Russell, 2001, *Molecular Cloning*, 3rd Ed. (Cold Spring Harbor Laboratory Press, Cold Spring Harbor, N.Y.); Ausubel et al., 1992, *Current Protocols in Molecular Biology* (John Wiley & Sons, including periodic updates); Glover, 1985, *DNA Cloning* (IRL Press, Oxford); Anand, 1992, *Techniques for the Analysis of Complex Genomes*, Academic Press, New York; Guthrie and Fink, 1991, *Guide to Yeast Genetics and Molecular Biology*, Academic Press, New York; Harlow and Lane, 1988, *Antibodies*, (Cold Spring Harbor Laboratory Press, Cold Spring Harbor, N.Y.); Jakoby and Pastan, 1979; *Nucleic Acid Hybridization* (B. D. Hames & S. J. Higgins eds. 1984); *Transcription And Translation* (B. D. Hames & S. J. Higgins eds. 1984); *Culture Of Animal Cells* (R. I. Freshney, Alan R. Liss, Inc., 1987); *Immobilized Cells And Enzymes* (IRL Press, 1986); B. Perbal, *A Practical Guide To Molecular Cloning* (1984); the treatise, *Methods In Enzymology* (Academic Press, Inc., N.Y.); *Gene Transfer Vectors For Mammalian Cells* (J. H. Miller and M. P. Calos eds., 1987, Cold Spring Harbor Laboratory); *Immunochemical Methods In Cell And Molecular Biology* (Mayer and Walker, eds., Academic Press, London, 1987); *Handbook Of Experimental Immunology*, Volumes I-IV (D. M. Weir and C. C. Blackwell, eds., 1986); Riott, *Essential Immunology*, 6th Edition, Blackwell Scientific Publications, Oxford, 1988; Hogan et al., *Manipulating the Mouse Embryo*, (Cold Spring Harbor Laboratory Press, Cold Spring Harbor, N.Y., 1986).

EXAMPLES

The present invention is described by reference to the following examples, which are offered by way of illustration and are not intended to limit the invention in any manner. Standard techniques well known in the art or the techniques specifically described below are utilized.

Example 1

Construction of the OV945 and Sequencing Verification

Based on an E2F-1 promoter sequence (GenBank S74230), primers 1405.77.1 (5'-ataccggtggtaccatccggacaaagcctgcgcg; SEQ ID NO:8) and 1405.77.2 (5'-agaceggtcgagggctcgatcccgctccg; SEQ ID NO:9) were designed and a 270 nt E2F-1 promoter (SEQ ID NO:1) was cloned from human genomic DNA by PCR. The AgeI (or PinAI) sites from the primers were used to replace the human uroplakin II promoter in CP1131 (U.S. Pat. No. 6,692,736, Zhang et al., Cancer Res. 2002 Jul. 1; 62(13):3743-50) with the E2F-1 promoter, resulting in plasmid CP1493. CP1493 has an E2F-1 promoter operatively linked to E1a, an IRES operatively linked to the E1b region and most of the E1B 19-KDa region deleted. The CP1493 plasmid was sequenced and confirmed as correct. CP1493 was cotransfected into 293 cells with pBHGE3 (from Microbix Biosystems, Inc. Toronto, Ontario, Canada and described in U.S. Pat. No. 6,140,087) to yield recombinant virus OV945. The structure of OV945 was confirmed by PCR amplification, followed by diagnostic enzymatic digestion for the corresponding specific regions. Further sequencing of the OV945 E1 region also confirmed the genomic structure (SEQ ID NO: 6).

Example 2

Construction of CG5757 and Sequencing Verification

The hTERT promoter was PCR cloned from plasmid pGRN316 (from Geron, Menlo Park, Calif.; also described in Günes et al., Cancer Research 60, 2116-2121, 2000) with primers 1244.39.1 (SEQ ID NO:10; aagtcgaccggtaccgtggcggagggactggggac) and 1244.39.2 (SEQ ID NO:11; aagtcgaccggtgcgggggtggccggggccaggg). The SalI cloning sites in the primers were used to replace the IRES fragment in CP1493 with the hTERT promoter. The derived plasmid, CP1509, has the E1a and E1B 55K genes under transcriptional control of the E2F and hTERT promoters, respectively. CP1509 was cotransfected into 293 cells with pBHGE3 (from Microbix Biosystems, Inc. Toronto, Ontario, Canada; described in U.S. Pat. No. 6,140,087) to yield recombinant virus. The nucleotide sequence of the left end of the CG5757 virus is provided (SEQ ID NO: 4).

Example 3

Construction of OV947 and Genomic Structure Verification

OV947 is structurally similar to CG5757 but lacks the E1B 19k deletion. The E2F-1 and hTERT promoters were derived from CP1509, a 0.27 Kb AgeI fragment and a 0.24 Kb SalI fragment, respectively. These promoters were cloned into CP686 (U.S. Pat. No. 6,692,736; Li et al., Cancer Res. 2001 Sep. 1; 61(17):6428-36) 5' to the E1A and E1B genes, respectively, to yield CP1498. The 0.27 Kb AgeI fragment (E2F-1 promoter) was cloned in place of the AFP promoter and the 0.24 Kb SalI fragment (hTERT promoter) was cloned in place of the IRES in CP686. The plasmid CP1498 was used to cotransfect with pBHGE3 (from Microbix Biosystems, Inc. Toronto, Ontario, Canada; U.S. Pat. No. 6,140,087) into 293 cells to yield OV947. The structure of OV947 (FIG. 1) was confirmed following PCR amplification and diagnostic enzymatic digestion for the corresponding specific regions.

Example 4

Construction of OV1025 and Genomic Structure Verification

The OV1025 virus has both E1A and E1B under transcriptional control of the hTERT promoter. In contrast to OV945 and CG5757, in OV1025, the E1B 19K region is not deleted. The AgeI sites in PCR primers 1244.39.1 (SEQ ID NO:10) and 1244.39.2 (SEQ ID NO:11) were used to clone the hTERT promoter in place of the AFP promoter in CP686 (U.S. Pat. No. 6,692,736, Li et al., Cancer Res. 2001 Sep. 1;

61(17):6428-36). The derived DNA construct CP1429 was cotransfected with pBHGE3 into 293 cells resulting in generation of the recombinant virus OV1025. The structure of OV1025 (FIG. 1) was confirmed by PCR amplification, followed by diagnostic enzymatic digestion of the corresponding specific regions.

Example 5

Cell Lines

Table 2 provides a listing of exemplary cell lines used to characterize the replication of the pan cancer viruses of the invention.

TABLE 2

Cell lines for evaluation of viruses.

| Cell Name | Cell Origin | ATTC | Notes |
|---|---|---|---|
| Hep3B | hepatocellular carcinoma | HB-8064 | |
| A549 | Lung carcinoma | CCL-185 | |
| LoVo | colorectal adenocarcinoma | CCL-229 | |
| SW480 | colorectal adenocarcinoma | CCL-228 | |
| LNCaP | Prostate cancer | CRL-1740 | |
| Panc-1 | Pancreatic cancer | CRL-1469 | |
| HeLa | Cervical epithelial adenocarcinoma | CCL-2 | |
| 253J BV | Human bladder transitional cell carcinoma | | Dr. Dr. Colin Dinney's Lab in M D Anderson Cancer Center |
| WI-38/VA-13 | SV40 transformed human lung fibroblast | CCL-75.1 | |
| HBL-100 | Normal breast cell | HTB-124 | ATCC discontinued |
| WI-38 | Human normal lung fibroblast cell | CCL-75 | |
| IMR-90 | Normal lung fibroblast cell | CCL-186 | |
| ARPE-19 | Normal retinal pigmented epithelial cell | CRL-2302 | |
| BSM | Bladder smooth muscle primary cell | | Human primary cell from Cambrex, East Rutherford, New Jersey |
| Lung FB | Primary lung fibroblast cell | | Human primary cell from Cambrex, East Rutherford, New Jersey |
| HMEC | Primary mammary epithelial cell | | Human primary cell from Cambrex, East Rutherford, New Jersey |
| HMVEC-L | Primary lung microvascular endothelial cell | | Human primary cell from Cambrex, East Rutherford, New Jersey |
| HRE | Primary renal epithelial cell | | Human primary cell from Cambrex, East Rutherford, New Jersey |
| SAEC | Primary small airway epithelial cell | | Human primary cell from Cambrex, East Rutherford, New Jersey |
| PrEC | Primary prostate epithelial cell | | Human primary cell from Cambrex, East Rutherford, New Jersey |

Example 6

Assay for Detecting Selective Expression of E1

Transcriptional control of the E1 gene is typically evaluated by Western blot. A sample virus is compared to wild type Adenovirus type 5 (designated OV802) for E1A and E1B expression 24 hours following infection (Multiplicity of infection (MOI) of 10 pfu/cell). In a typical study, about 25 ug of cell lysate from each sample is subjected to immunostaining by mouse monoclonal antibodies against E1A or E1B and visualized by ECL.

Example 7

Tumor Selective Cytotoxicity Assays

Cytopathic Effect & Crystal Violet Assay: In a typical study cancer cells (Hep3B, LoVo, A549, 253J B-V) and normal cells (HRE, HMVEC-L and WI-38 cells) are tested in a crystal violet assay for cell killing. Briefly, the cells are plated in 5well plates. One day later the cells are infected with CG5757 or OV802 at various MOIs of 10, 1, 0.1, 0.01, 0.001 and 0 PFUs per cell. At a selected time point(s) after the infection, cells are observed microscopically for CPE. Then cells are fixed with 10% Formalin and stained with 1% Crystal Violet using standard procedures and the amount of staining is observed.

MTT Assay: In a typical study, cells are plated on 96-well plates at 10,000 cells/well one day prior viral infection. Cells are infected at different MOIs (pfu/cell) for selected time points and viral cytotoxicity is determined by percentage of control in the MTT assay as previous described (Li et al., 2001). The cytotoxicity data is analyzed for sigmoidal dose response curve fit using GraphPad software and the LD50 determined. Comparing the relative LD50 between tumor and normal cells, the cytotoxic specificity of an oncolytic vector is represented by the selectivity index (SILD). The formula for SILD is (($LD_{50}$ of Ad5 on tumor)/($LD_{50}$ of oncolytic virus on tumor))/(($LD_{50}$ of Ad5 on normal)/($LD_{50}$ of oncolytic virus on normal)). Relative LD50 (OV802/oncolytic vector) values of 1 indicate the vector has the identical cell killing as wild type OV802. SILD values above "1" indicate tumor cell selectivity.

Ex Vivo Primary Tumor Culture Assay: In a typical study, samples of primary human tumors or normal tissue were collected from patients who had undergone surgical resection for colorectal cancer or pancreatic cancer. Tissue samples were quickly placed in an ice-cold solution appropriate culture medium, dissected on ice and homogeneous tissue slices were selected. Cube-sized pieces of each tissue sample were prepared, rinsed and placed in medium suitable for viral infection. A known amount of wild type adenovirus or recombinant viral vector was added. After two hours, the culture medium was replaced with fresh medium supplemented with insulin and hydrocortisone. The tissue samples were placed on Millicell membrane culture inserts (0.45 □M pore size; Millipore, Billerica, Mass.) placed inside each well of a 6-well plate and incubated under appropriate conditions. The tissue samples were examined by immunohistochemical staining using an adenoviral-specific antibody at 24 hours post-infection using standard procedures or harvested at day 5 post-infection for $LD_{50}$ determination of progeny viruses after a specified number of freeze-thaw cycles. The SILD was then calculated from normal tissue and tumor tissue as described above. SILD values of greater than "1" indicate tumor cell selectivity.

Ex

Vivo Primary Tissue Culture Assay

Example 8

A Viral Production and Growth Kinetics Assay for Oncolytic Adenoviruses

In a typical study, cells are plated on 6-well plates at 5E5 cells/well one day prior virus infection. Oncolytic virus and OV802 are infected at MOI of 2 (pfu/cell) for a selected amount of time, for example 72 hours. Cell lysates are harvested and plaque titered on 293 cells. For a growth kinetics study, infected cells are harvested and titrated at corresponding time points.

Example 9

In Vivo Antitumor Efficacy

A549 xenograft model: In a typical study, six-to-eight weeks old athymic BALB/C nu/nu mice are used. Generally, $5 \times 10^6$ A549 cells in 0.1 ml are mixed with 0.1 ml of Matrigel and injected into each animal subcutaneously. Nude mice bearing subcutaneous A549 tumors are injected intratumorally at a dosage of about $4 \times 10^8$ viral particles/mm$^3$. Virus may be injected on more than one day depending upon the regimen. Tumor volume and body weight are monitored and statistically analyzed using Prism GraphPad.

253JB-V xenograft model: In a typical study, six-to-eight weeks old athymic BALB/C nu/nu mice are used. About 2E6 253J B-V cells in 0.1 ml are mixed with 0.1 ml of Matrigel and injected to each animal subcutaneously. Nude mice bearing subcutaneous 253J B-V tumors are injected intratumorally at a dosage of about $4 \times 10^8$ viral particles/mm$^3$ for four consecutive days beginning at day 20. Tumor volume and body weight are monitored and statistically analyzed using Prism GraphPad.

Example 10

CG5757—Selective Expression of E1

The following example demonstrates that the specific expression of the E1A and E1B genes in CG5757 results in viral replication and cell killing.

Using the procedure described in Example 6, the normal lung fibroblast cell WI-38 (ATCC #CCL-75) (Rb+) was compared to the isogenic WI-38/VA-13 cell (ATCC #CCL-75.1). WI-38/VA-13 was transformed by SV40 and therefore has a defective Rb-pathway. During infection, wild type OV802 showed no selectivity for relative E1 expression in WI-38/VA-13 cells. In comparison, CG5757 only expressed detectable E1 in Rb defective VA13 cells. This selective E1 expression indicates that CG5757 is under the transcriptional control of the E2F-1 promoter. The control of the E1B 55K gene in CG5757 was also demonstrated to be cancer-specific in that it is only detected in infected cancer cells but not normal HRE cells. Therefore, the observed expression of both E1A and E1B genes following infection with CG5757 is tumor-specific and the viral replication is selective for cancer cells that are Rb-defective and telomerase positive. To demonstrate the tumor selectivity of CG5757, a broad panel of cancer cell lines (Hep3B, LoVo, A549, 253J B-V, Panc-1, and Hela) and normal cells (HRE and WI-38) were analyzed for E1A expression after viral infection. CG5757 induced E1A expression was only detected in the cancer cells. CG5757 clearly demonstrated tumor-selective expression of both the E1A and E1B genes, the products of which play an essential role in activating other adenoviral genes.

Example 11

CG5757 In Vitro Tumor Selective Cytotoxicity

The cytopathic effect induced following infection in different cells with wild type adenovirus OV802 and the tumor selective CG5757 virus was compared by both microscopy and crystal violet staining. OV802 showed no selectivity for killing of cancer versus normal cells, whereas infection with CG5757 resulted in cytolysis (killing) specific to cancer cells. CG5757 showed 1,000 to 10,000 fold less infectivity relative to OV802 in normal cells.

Figure 3:
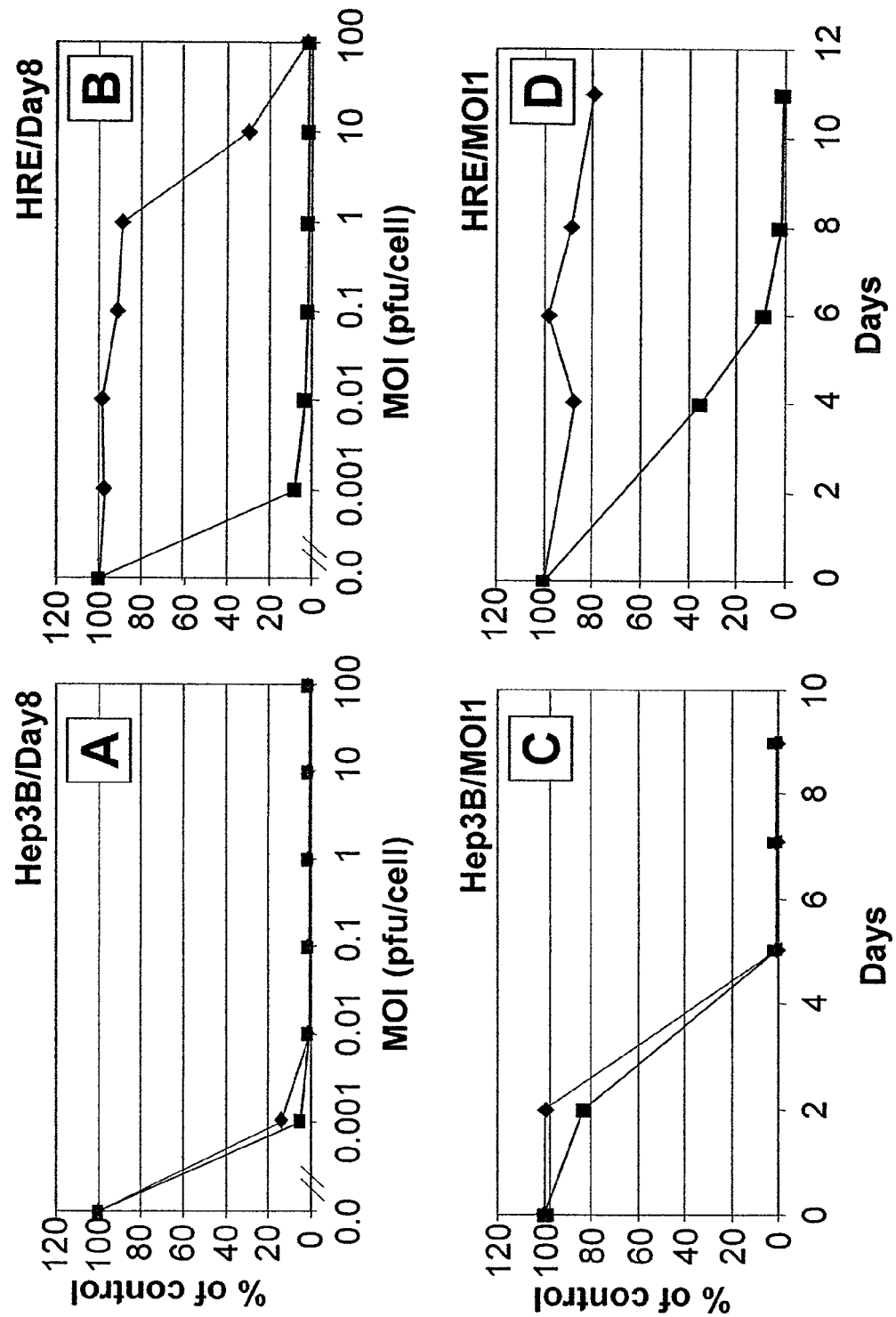
FIGS. 3A-D shows the results of a MTT cytotoxicity assay performed with CG5757 compared to wild-type adenovirus type 5 (OAV802) on Hep3B and HRE cells. Cells were infected with viruses at different doses and subjected to MTT assay at selected times. The viral cytotoxicity is represented as percentage of the uninfected cell control. OAV802 is graphed as squares and CG5757 is graphed as diamonds. The graphs show cytotoxicity after infection as measured by MTT assay and graphed as a percentage compared to the uninfected cells.

An in vitro MTT assay was also used to quantitatively compare the cytotoxicity of CG5757 and wild type Ad5 (OV802) on different cells. In the tested cancer cells, CG5757 performed similarly to wild type Ad5 in a dose response study (FIG. 3). At a selected MOI of, for example, 1 pfu/cell (FIG. 3 panels C and D), CG5757 exhibited the same killing kinetics as wild type Ad5 in Hep3B cells. Furthermore, the cytotoxicity data were analyzed for Sigmoidal dose response curve fit using GraphPad software and the LD50 determined. The comparison of the LD50 value between wild type adenovirus, OV802, and the oncolytic vector, CG5757, indicated the strength of viral cytotoxicity and can be used to normalize the transduction efficiency of different cells. Table 3 lists the SILD of CG5757, that is the LD50 of CG5757 relative to Ad5 on primary cells (HRE, PrEC, HMEC, HMVEC-L, BSM, Lung FB, SAEC, WI-38 and tumor cells (Hep3B, A549, LoVo, SW480, LNCap, Panc-1, Hela and 253J B-V) using the SILD formula. SILD values above "1" indicate tumor cell selectivity.

TABLE 3

Selectivity index of CG5757

|         | HRE     | PrEC    | HMEC  | HMVEC-L | BSM   | Lung FB | SAEC  | WI-38 |
|---------|---------|---------|-------|---------|-------|---------|-------|-------|
| Hep3B   | 1676.74 | 6957.82 | 85.50 | 154.79  | 75.76 | 2.27    | 62.99 | 75.76 |
| A549    | 84.14   | 349.13  | 4.29  | 7.77    | 3.80  | 0.11    | 3.16  | 3.80  |
| LoVo    | 340.18  | 1411.60 | 17.35 | 31.40   | 15.37 | 0.46    | 12.78 | 15.37 |
| SW480   | 571.53  | 2371.64 | 29.14 | 52.76   | 25.83 | 0.77    | 21.47 | 25.82 |
| LNCaP   | 115.65  | 479.88  | 5.90  | 10.68   | 5.23  | 0.16    | 4.34  | 5.23  |
| Panc-1  | 118.55  | 491.93  | 6.05  | 10.94   | 5.36  | 0.16    | 4.45  | 5.36  |
| Hela    | 1731.10 | 7183.40 | 88.28 | 159.81  | 78.22 | 2.34    | 65.04 | 78.22 |
| 253J B-V| 278.22  | 1154.52 | 14.19 | 25.68   | 12.57 | 0.38    | 10.45 | 12.57 |

Based on the selectivity index derived from the cytotoxicity assay using a variety of different cells, 57 of 64 comparisons of the relative cytotoxicity of CG5757 and wild type Ad5 between tumor and normal cell lines yielded a selectivity index greater than 1, demonstrating strong tumor selectivity.

Tissue-specific viral expression and production of CG5757 in clinically derived tissue samples were determined using the ex vivo primary tumor culture model of Example 7.

Following the procedure in Example 7, tissue samples isolated from primary human tumors or normal tissue and quickly placed in an ice-cold solution of Iscove's modified Dulbecco's medium (IMDM) supplemented with 10% fetal calf serum (FCS) and 100 □g/ml penicillin and streptomycin. Tissue samples were dissected on ice, homogeneous tissue slices were selected and 1 mm$^3$ cubes of each tissue sample were prepared, rinsed and placed in 6-well plates in IMDM supplemented with 5% FCS. An aliquot of 1×10$^9$ pfu of CG5757 or Ad5 (also known as OV802) was added to the appropriate tissue-containing well. After two hours, the culture medium was replaced with fresh IMDM supplemented with 5% FCS 10 □M insulin and 1 □M hydrocortisone. The tissue samples were placed on Millicell membrane culture inserts (0.45 □M pore size; Millipore, Billerica, Mass.) placed inside each well of a 6-well plate and incubated at 37° C. in a 5% $CO_2$ atmosphere. At day 5 post-infection, the medium and infected tissue were collected and subjected to three freeze-thaw cycles. The lysates were titrated on 293 cells and the $TCID_{50}$ titers were calculated for each sample.

The results demonstrate that an average more than 10-fold more CG5757 was detected in tumor colon tissues than in adjacent normal tissues. For instance, the primary tumor isolated from one patient had about 10,000-time higher infectious CG5757 present in tumor tissue than the normal tissue. In contrast, there was no significant difference in virus production between tumor or normal tissues following wild-type Ad5 infection. To evaluate tumor selectivity of virus production, the $TCID_{50}$ of CG5757 was compared to that of Ad5 within the same pair of tissues to control for differences in infectivity and viral production to generate the Selectivity Index, as calculated above. The Selectivity Index obtained from each of the various primary tumors ranged from about 4 to greater than 3000, with the majority of samples having a Selectivity Index of greater than 75.

Tissue-specific viral expression was also demonstrated by immunohistochemical staining. Following the procedure in Example 7, a portion of the primary tumor samples infected with CG5757 or wild type Ad5 was analyzed 24 hours post-infection for expression of Ad E1A using an anti-E1A antibody. The results show that E1A expression was detectable only in colon tumor tissues but not in the normal tissues such as colon, pancreas and spleen. These results demonstrate that the E2F-1 promoter is active in and selective for primary colon tumors. Preferential viral production of CG5757 in tumor tissue was observed in tissues samples collected from multiple patients.

These results from the ex vivo experiments using clinical primary tissues provide further evidence of the high tumor selectivity of CG5757.

Results Ex Vivo Model

Example 12

OV945 and OV947 In Vitro Tumor Selective Cytotoxicity

Figure 8:
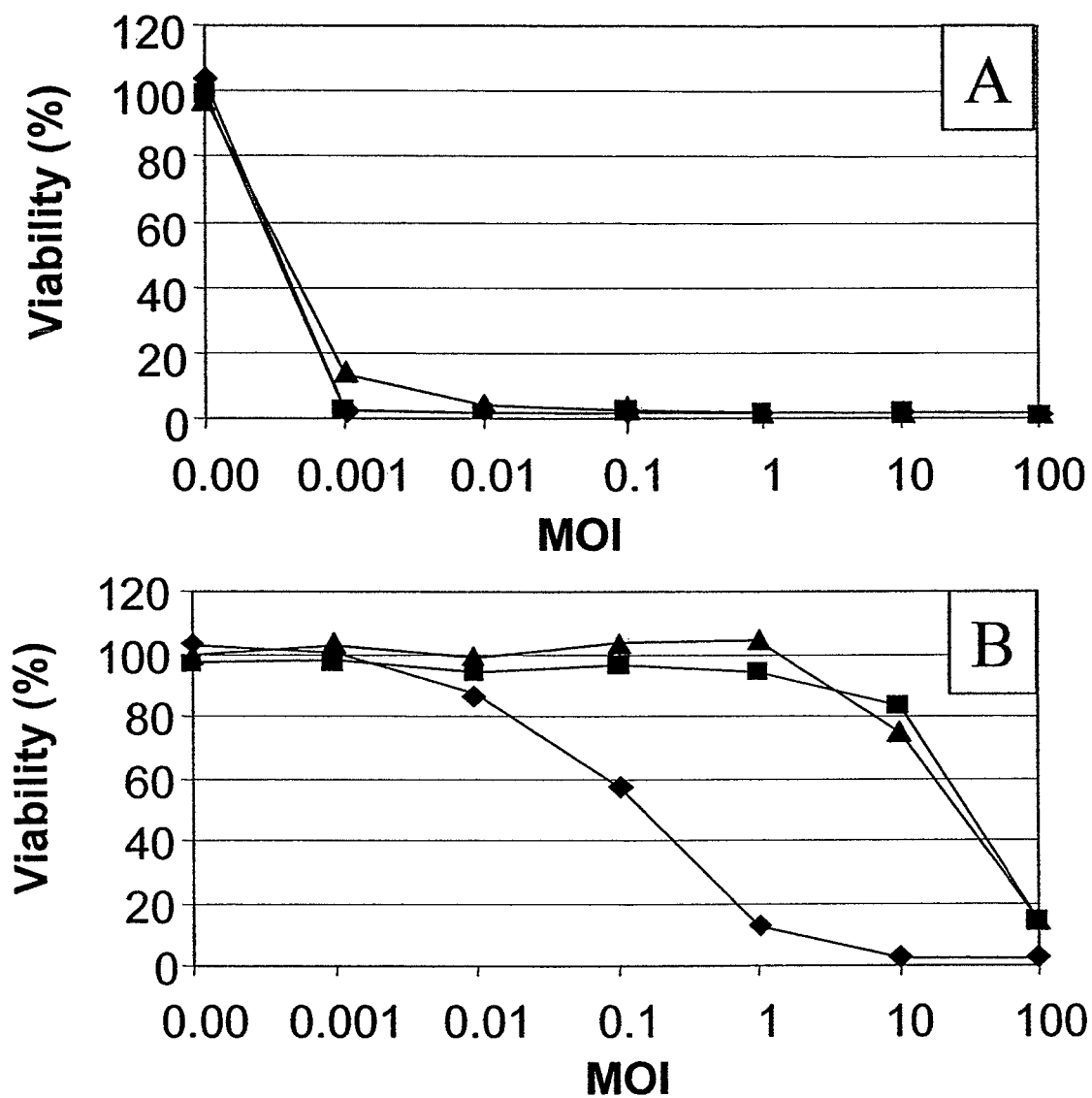
FIG. 8 shows results from an MTT assay with the viruses OV945 (squares), OV947 (diamonds) and OV802 (triangles) tested on the Hep3B cell line (A) and BSM cell line (B). Cells were harvested on the $10^{th}$ day after infection for the MTT assay.
Figure 9:
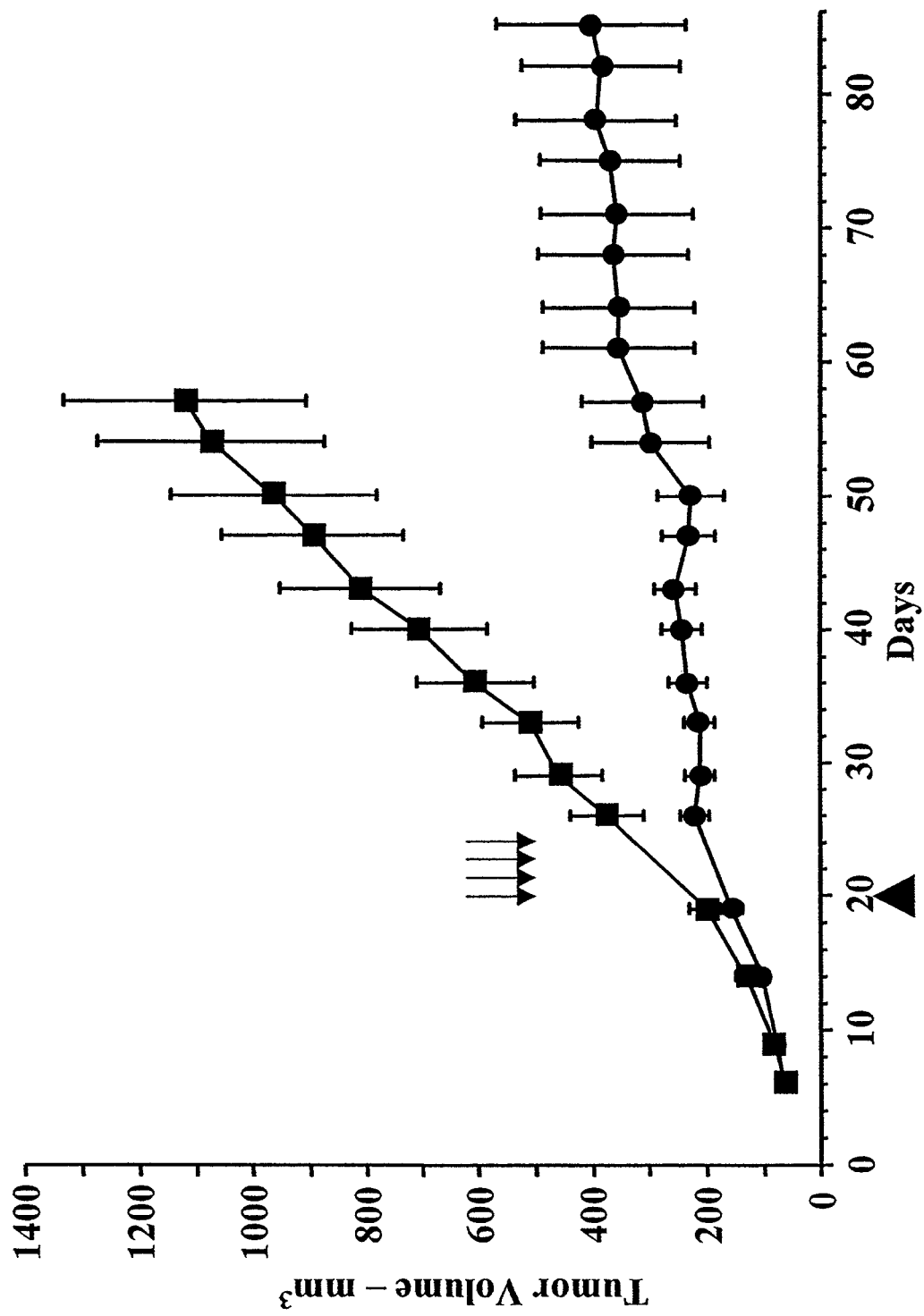
FIG. 9 shows tumor growth inhibition of an A549 xenograft model infected with CG5757. Tumors were injected with CG5757 (circles) on days 20, 21, 22 and 23 after tumor implantation or were injected with PBS-glycerol control (squares).

Using an MTT assay, the in vitro tumor selective cytotoxicity of OV945 and OV947 was evaluated on Hep3B and BSM cells. The results are shown in FIG. 8. The Cytopathic Potency Index is the relative LD50 by ratio of LD50 of OV802 over LD50 of the test viral vector on a selected cell (Johnson et al., 2002, Cancer Cell, 1:325-337). As listed in Table 4, both of the test viruses had essentially the same potency on the tumor cell line Hep3B as OV802. On the other hand, the sample viruses were both about 333-fold less potent on the normal cell line, BSM.

TABLE 4

Cytopathic Potency Index

|            | OV802 | OV945 | OV947 |
|------------|-------|-------|-------|
| Hep3B cells| 1     | 1     | 1     |
| BSM cells  | 1     | 0.003 | 0.003 |

Example 13

In Vitro Tumor Selective Cytotoxicity for CG5757, OV945 and OV947

The Crystal Violet Assay was also used to evaluate CV945 and CV947. OV802 was used as a control. Tumor cells, Hep3B, A549 and LoVo, were infected at an MOI of 1 pfu/cell. Normal cells, Lung FB, IMR90 and WI-38, were infected at an MOI of 10 pfu/cell. All infections were performed in triplicate. Six days after infection with CV945, CV947 or OV802, for each of the tumor cell lines, most if not all of the cells displayed CPE. In contrast, the normal cells infected CV945 and CV947 displayed little, if any, CPE, but normal cells infected with OV802 displayed complete CPE. Cells were then stained with crystal violet. The tumor cells infected with any of three viruses displayed very little staining. Whereas, the normal cells displayed staining over the majority of the surface except for those infected with CV802, which displayed very little staining.

The in vitro cytotoxicity MTT assay was used to compare oncolytic vectors to the wild type OV802. Table 5 summarizes the LD50 values following MTT assay in different cells.

TABLE 5

Comparison of LD50 (pfu/cell) on different cells

|       | Hep3B  | A549   | LoVo   | SW480  | LNCaP  | Panc-1 | HRE    | PrEC     |
|-------|--------|--------|--------|--------|--------|--------|--------|----------|
| OV802 | 0.0003 | 0.0008 | 0.0124 | 0.0146 | 0.0018 | 0.0030 | 0.0006 | 0.0184   |
| CG5757| 0.0011 | 0.0577 | 0.2275 | 0.1601 | 0.0948 | 0.1590 | 3.6946 | 477.0356 |
| OV945 | 0.0017 | 0.0135 | 0.0412 | 1.0753 | 0.8655 | 0.0806 | 0.9781 | 0.5058   |
| OV947 | 0.0311 | 0.1923 | 0.4903 | 1.1968 | 0.7299 | 1.3509 | 1.3710 | 16.9500  |

Example 14

The Tumor Selective Production of CG5757

Figure 4:
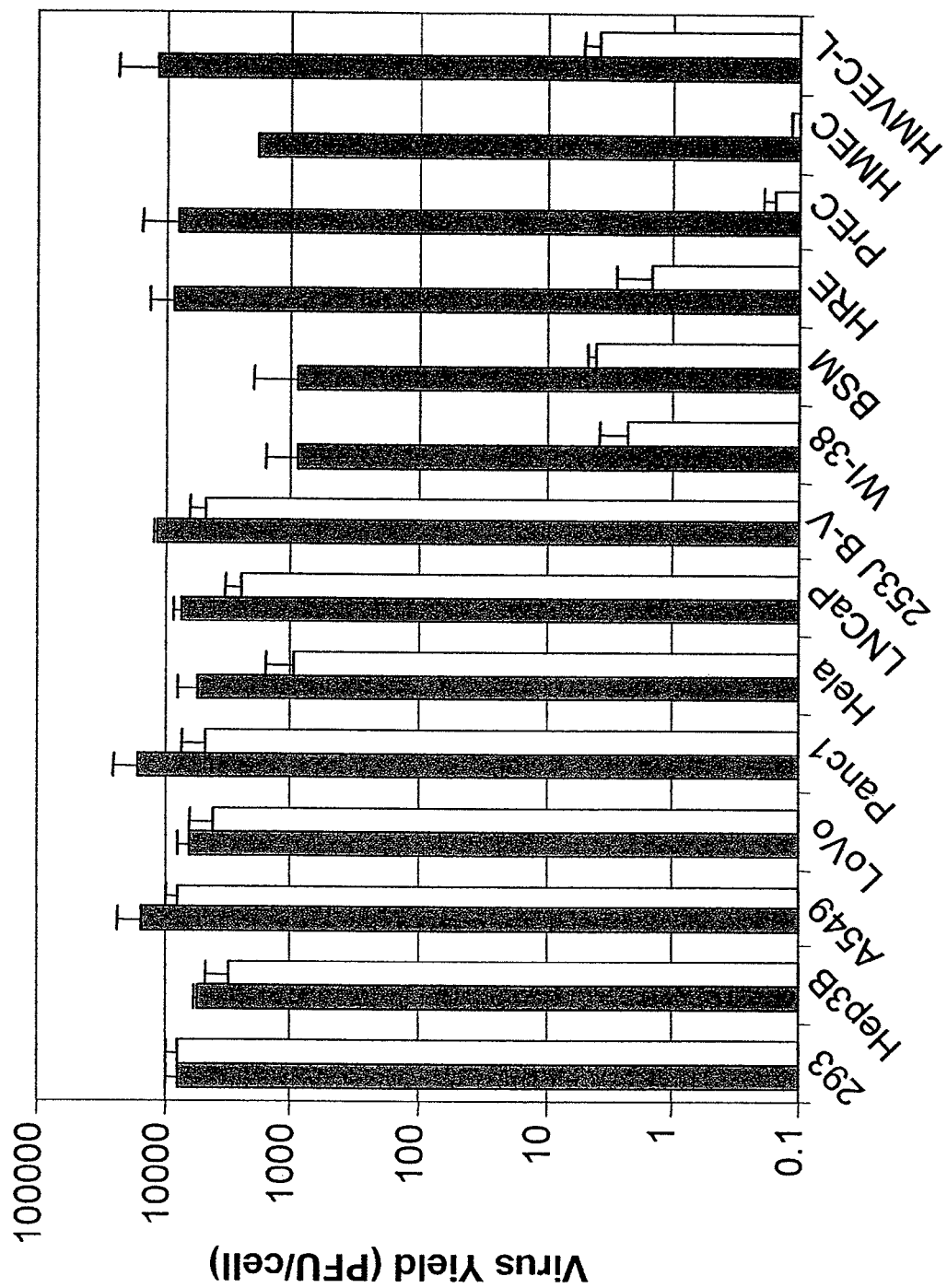
FIG. 4 shows selective production of CG5757 on different cell lines. Various cell lines were infected with CG5757 (white bars) or OV802 (black bars) at an MOI of 2 (pfu/cell) for 72 hours. The cell lysates were harvested and plaque titrated on 293 cells.
Figure 5:
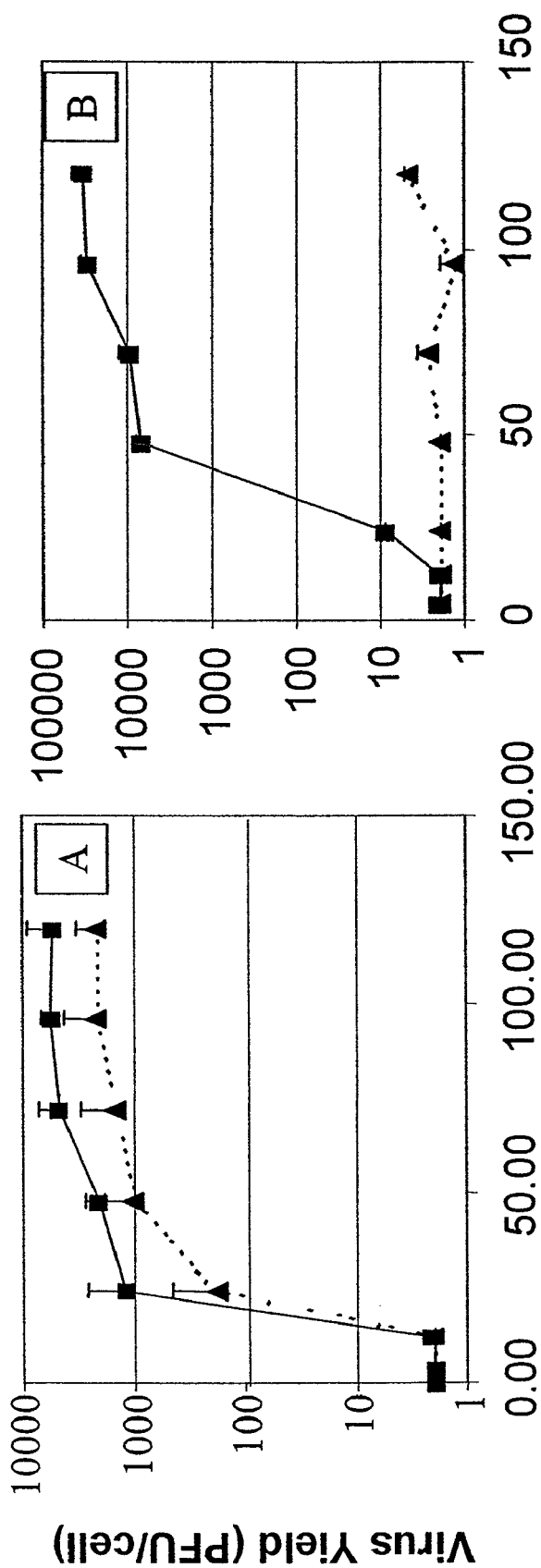
FIG. 5 shows the results of a growth kinetics study. CG5757 (triangles) and OV802 (squares) were infected on Hep3B cells (FIG. 5A) or HRE cells (FIG. 5B) at an MOI of 2 (pfu/cell) for selected times. Infected cells were harvested and titered for the corresponding time points on 293 cells

Using the procedure described in Example 8, in vitro selective replication of CG5757 was compared to wild type virus by burst size (viral production) and growth kinetics assay in a panel of tumor and normal cells (FIGS. 4 and 5). In the burst size assay, all cells were infected at an MOI of 2 pfu/cell for 72 hrs and harvested for plaque titration on 293 cells (FIG. 4). For the growth kinetic study, infected cells were harvested and titrated at corresponding time points (FIG. 5). CG5757 showed selective replication in the tumor cells at a level comparable to wild type OV802. On the normal cells, the burst size was about 1,000 to 100,000 fold lower than that of wild type OV802. Further viral growth curves on Hep3B and HRE cells (FIG. 5) also indicate that CG5757 replicates similarly to wild type OV802 in the cancer cells, but not in the normal cells.

Figure 6:
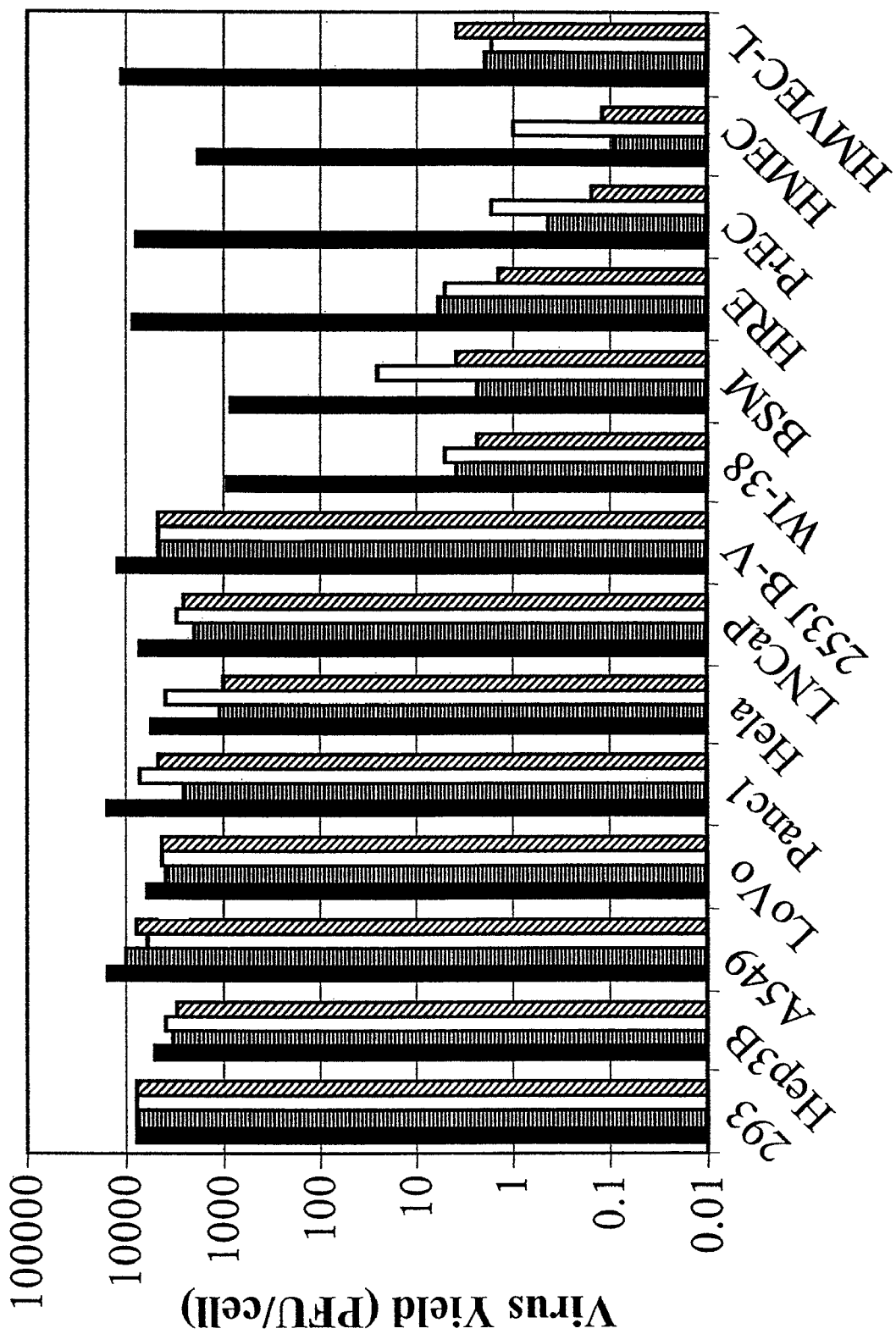
FIG. 6 shows selective production of OV945 (gray bars), OV947 (white bars) and CG5757 (slanted striped bars) as compared to OV802 (black bars) on different cells.

The same analysis was performed for the viruses OV945 and OV947. On the normal cells, the burst size was about 1,000 to 100,000 fold lower for OV945, OV947 and CG5757 than that of wild type OV802 (FIG. 6).

Example 15

The Tumor Selective Production of OV945 and OV947

Figure 7:
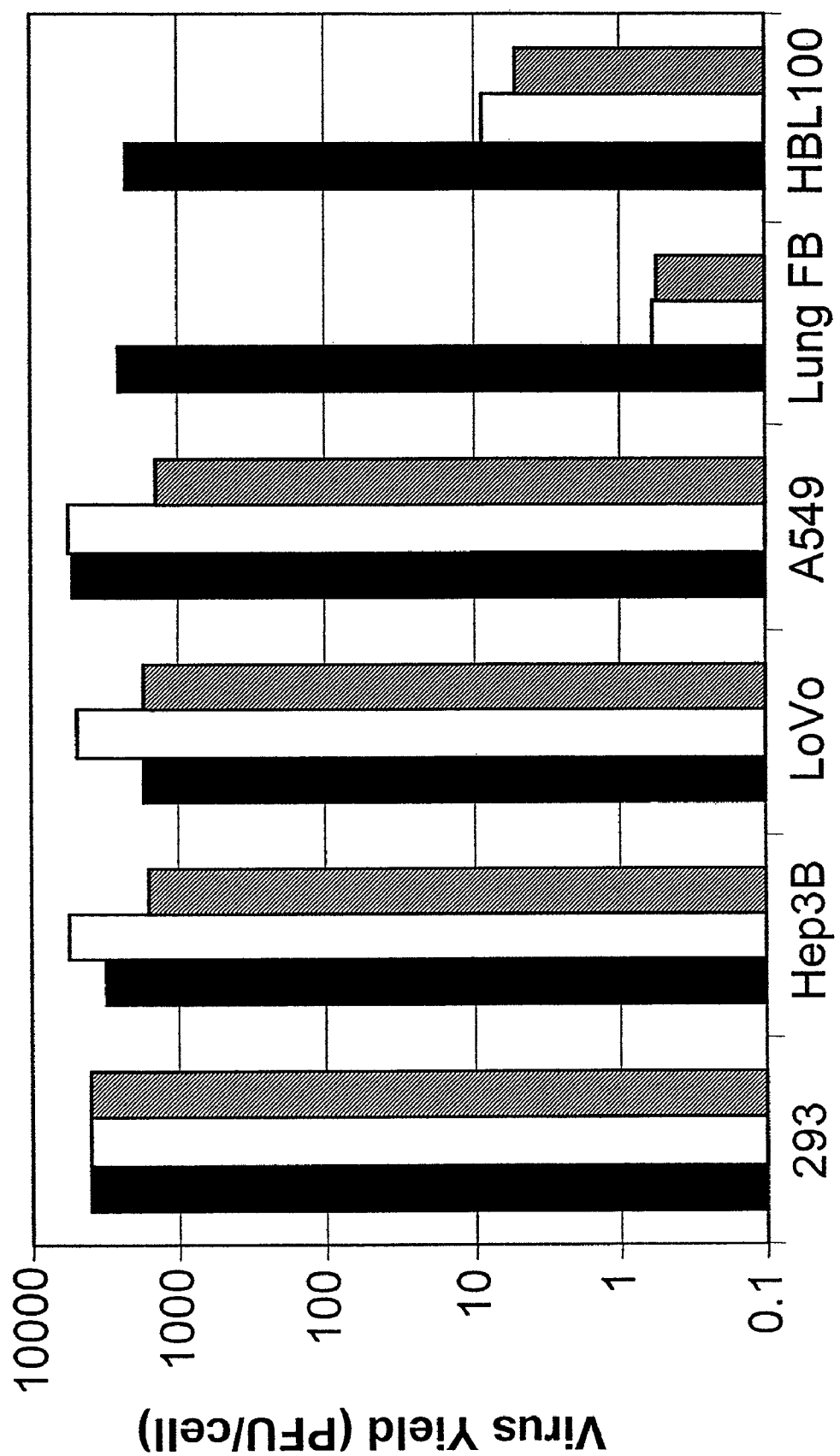
FIG. 7 shows selective production of OV945 (white bars) and OV947 (gray bars) compared to OV802 (black bars) on different cells.

Using the procedure described in Example 8, in vitro selective replication of OV945 and OV947 was compared to wild type virus by burst size (viral production) on various cells, including HBL 100 cells. See FIG. 7.

Example 16

CG5757 and OV945—In Vivo Antitumor Efficacy

In vivo antitumor efficacy of CG5757 and OV945 was determined using the procedures described in Example 9. CG5757 was tested in an A549 xenograft model. CG5757 was injected on days 20, 21, 22, and 23 after tumor implantation. FIG. 13 shows that the treatment group (n=10) demonstrated significant anti-tumor efficacy relative to the control group (n=10) ($p<0.01$ by Dunnette's method of ANOVA with PBS/glycerol as the control group). With a total viral dose as high as $1.6 \times 10^{13}$ viral particles per kilogram of body weight, there was no body weight change as compared to the control group.

Figure 2:
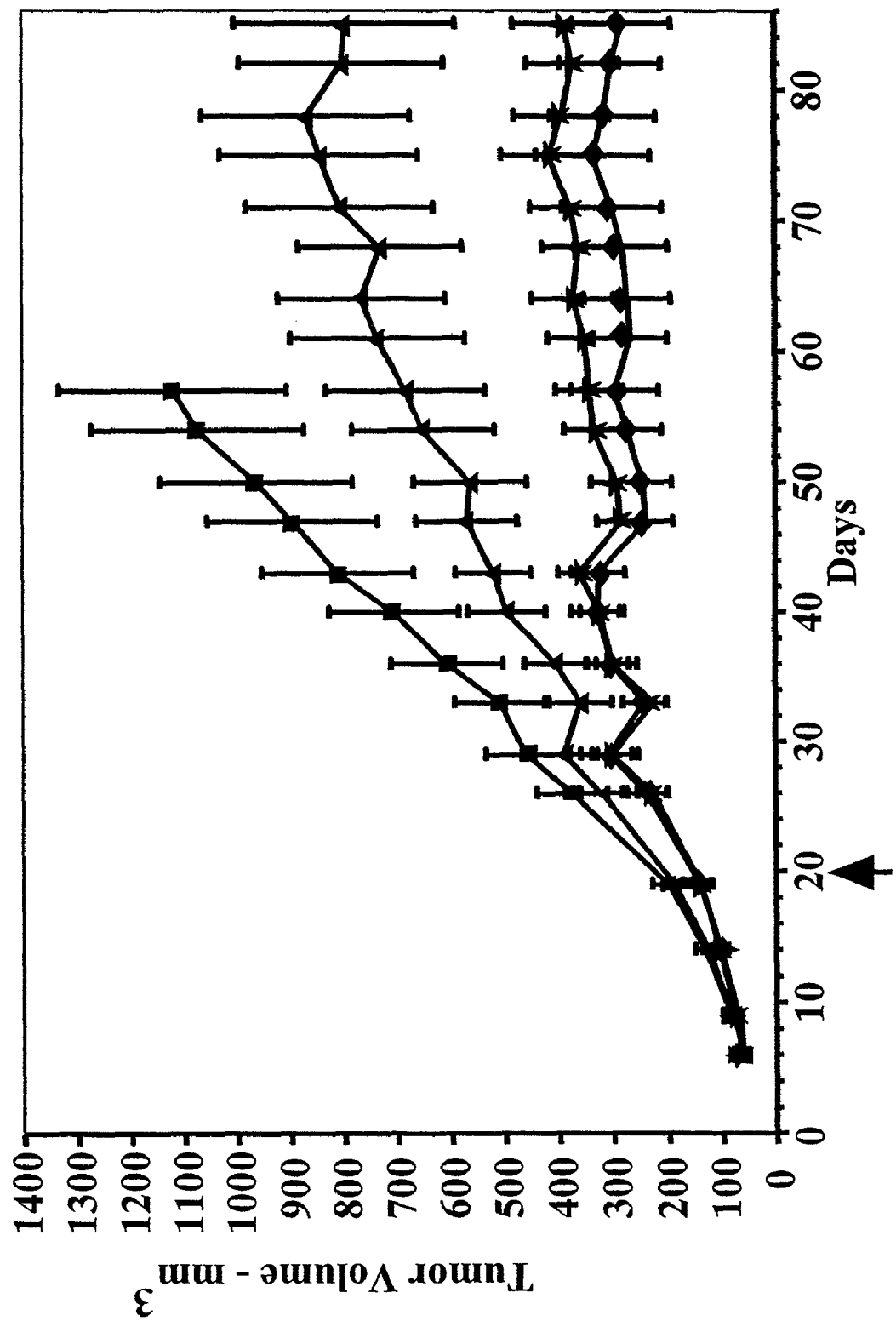
FIG. 2 shows tumor growth inhibition of an A549 xenograft model infected with OV945. Tumors were injected with OV945 on the following days after tumor implantation: Regimen #1: 20, 21, 22, 23 (Triangles); Regimen #2: 20, 23, 26, 29 (Stars); Regimen #3: 20, 27, 34, 41 (Diamonds). Another set of tumors was treated with a PBS-glycerol control (Squares) by regimen 2.

The A549 model was also used to demonstrate the antitumor efficacy of OV945. After intratumoral administration of OV945, the treatment group demonstrated a statistically significant inhibitory effect on the tumor growth as compared to the control group (FIG. 2). The body weight also had no significant change indicating the toxicity after intratumoral injection is minimized.

Similar studies were done using nude mice bearing subcutaneous 253J B-V tumors. CG5757 or OV945 was administered by intratumoral injection of $4 \times 10^8$ vp/mm$^3$ at various dosing regimens.

Figure 10:
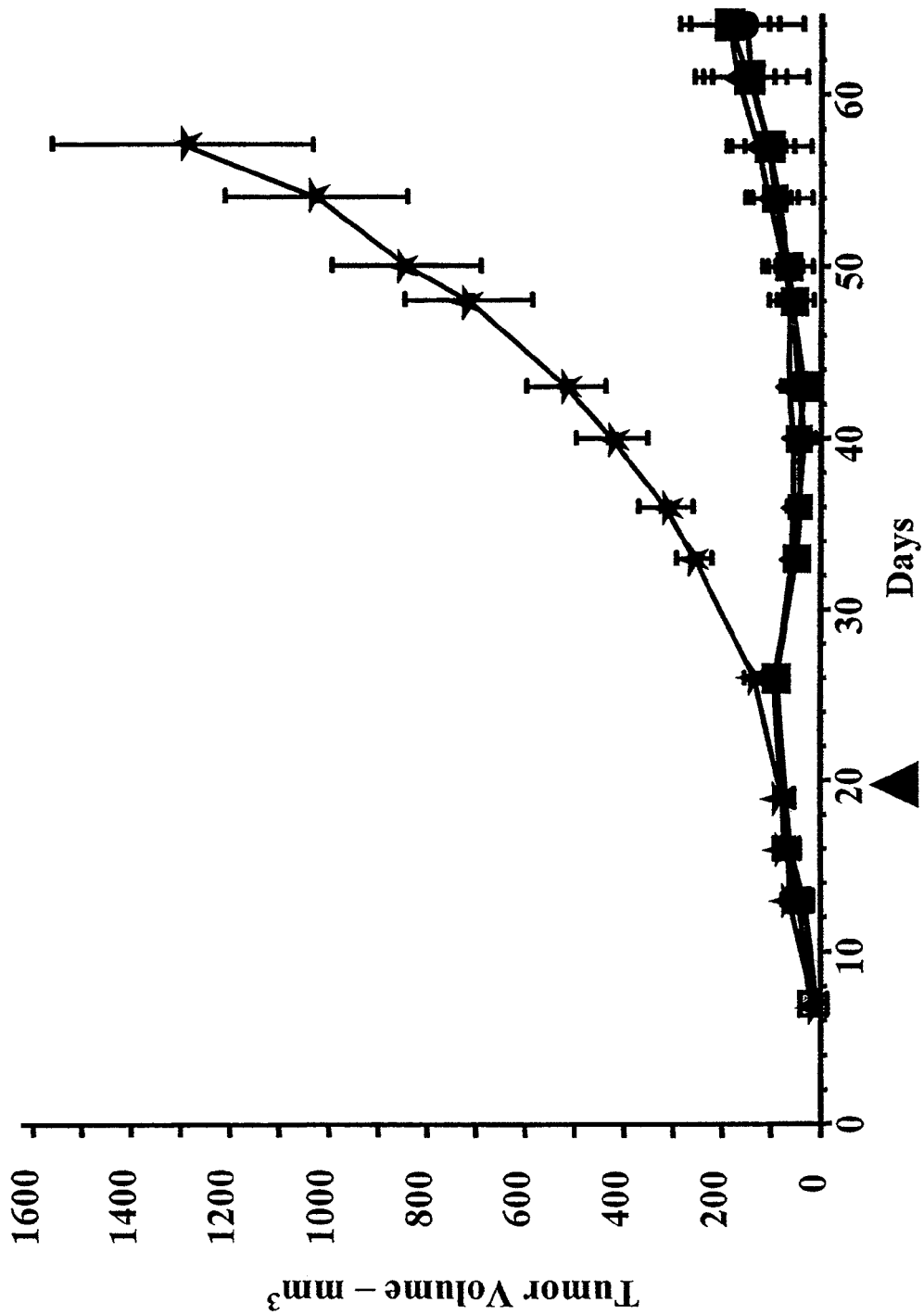
FIG. 10 shows tumor growth inhibition of a 253J B-V xenograft model infected with CG5757. Tumors were injected with CG5757 on the following days after tumor implantation: Regimen #1: 20, 21, 22, 23, 24 (Circles); Regimen #2: 20, 24, 27, 30 (diamonds); Regimen #3: 20, 27, 34, 41 (Triangles). Another set of tumors was treated with a PBS-glycerol control (Stars) according to Regimen #2.

For CG5757, three different regimens were carried out and tumors were injected on the following days after tumor implantation: Regimen 1: 20, 21, 22, 23, 24; Regimen 2: 20, 24, 27, 30; Regimen 3: 20, 27, 34, 41. All of the CG5757 treatment groups in different regimens had significant tumor regression compared to the controls ($p<0.01$ by Dunnette's method of ANOVA with PBS/glycerol as the control group). See FIG. 10. Four weeks after treatment, the average volume of 253J B-V tumors in animals treated with five consecutive daily intratumoral injections of CG5757 ($4 \times 10^8$ particles/mm$^3$ of tumor) decreased to 72% of baseline while the control group had an increase to 944% of baseline. Furthermore, about 50% of animals in each treatment group had complete regression of the 253J B-V tumor xenografts, suggesting strong antitumor efficacy of CG5757.

Figure 11:
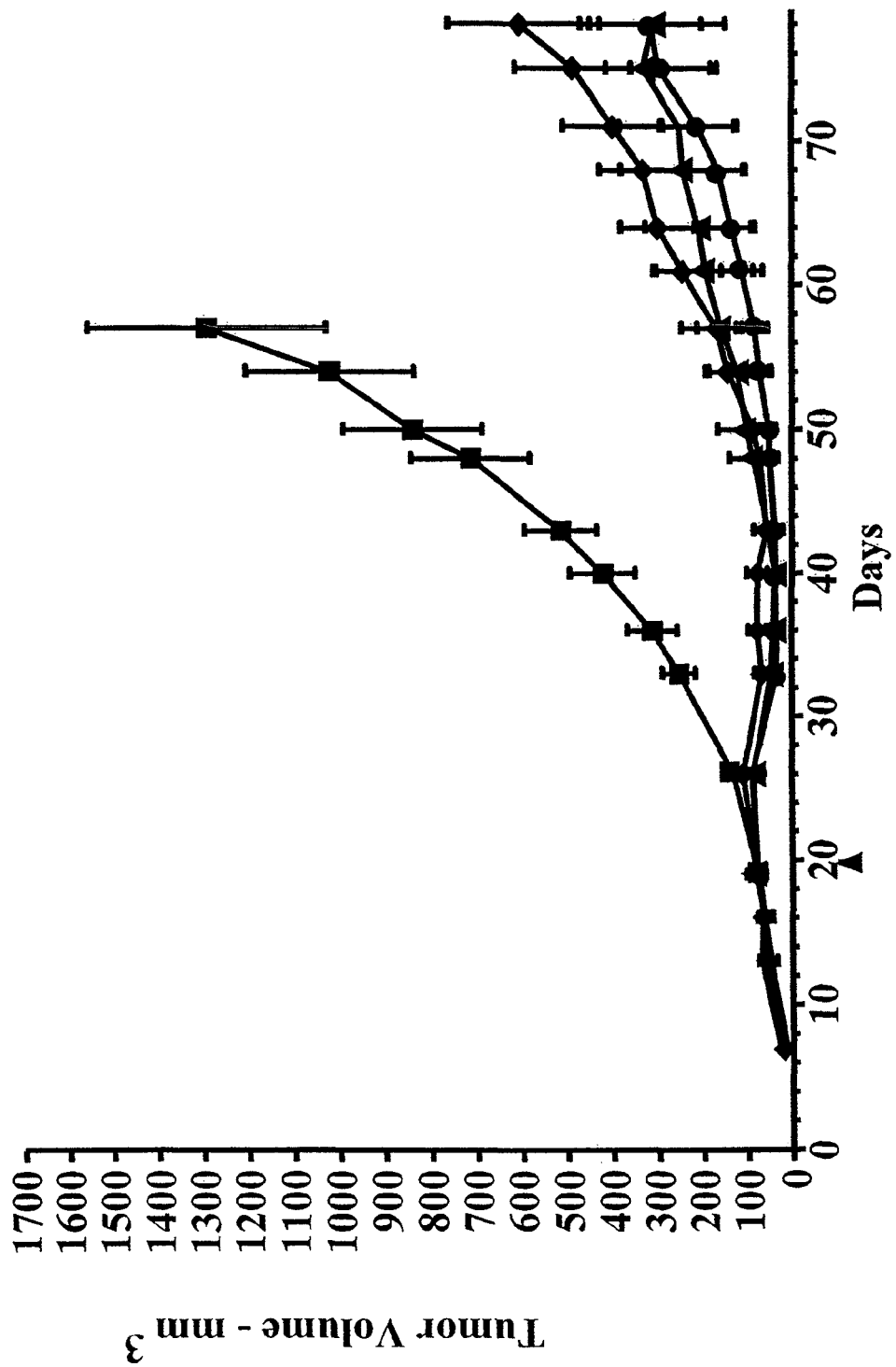
FIG. 11 shows tumor growth inhibition of a 253J B-V xenograft model infected with OV945. Tumors were injected with OV945 on the following days after tumor implantation: Regimen #1: 20, 21, 22, 23, 24 (Triangles); Regimen #2: 20, 24, 27, 30 (Circles); Regimen #3: 20, 27, 34, 41 (Diamonds). Another set of tumors was treated with a PBS-glycerol control (Squares) following regimen #2.

For OV945 tested in the 253J B-V tumor model, the results are shown in FIG. 11.

Example 17

CG5757: In Vivo Toxicity Assay

The in vivo toxicity profile of CG5757 was compared to wild-type Ad5 and the replication defective Addl312 in immune-deficient SCID mice following intravenous administration. SCID mice were injected with a single intravenous dose of $8.5 \times 10^{11}$ vp/kg of CG5757, wild-type Ad5, replication defective Addl312, or PBS supplemented with 10% glycerol (vehicle control) and animals were closely monitored. No morbidity was seen in the vehicle, Addl312 or CG5757 treatment groups.

Individual body weights were collected over a 28 day period and compared among the different treatment groups. Relative to study day 1, all treatment groups had no body weight gain between day 3 and day 8. Ad5 treated animals lost weight steadily between day 1 and day 5, at which time they became moribund and were terminated. In contrast, the CG5757 treatment group gained body weight after the initial loss between day 3 to 8, and the difference in mean body weight change for this group was not significant compared to the vehicle or Addl312 treated groups.

In addition, selected clinical chemistry parameters were monitored on study day 2, 4, 14 and 28. During the course of the study, observed levels of creatine kinase (CK) were not different between any treatment group at any time point, indicating that there was no overt toxicity in skeletal muscle, cardiac muscle, brain, or kidney (FIG. 4B and data not shown). Furthermore, serum levels of alanine aminotransferase (ALT) and aspartate aminotransferase (AST) was evident on day 2 and showed no difference between any treatment group; however, significantly elevated AST and ALT levels ($p<0.05$) were seen in mice treated with wt Ad5 (OV802) on day 4 compared to control or Addl312 treatment groups. The CG5757 treatment group had an elevation of both ALT and AST on study day 4, however, there was no significant difference relative to vehicle or Addl312 treated mice. By day 14, all serum parameters returned to normal Taken together, these observations demonstrate that CG5757 is less toxic than wild-type Ad5 and, therefore, may have potential as a therapeutic agent.

Example 18

In Vitro Combination of CG5757 and Chemotherapeutic Agents

Potential synergism between existing chemotherapeutic agents and the replication competent vectors of the present invention was investigated. Co-application of CG5757 with a variety of known chemotherapeutic agents was evaluated using an in vitro cell assay. A variety of known chemotherapeutic agents were tested in combination with CG5757 for their in vitro cytotoxic effect on Hep3B and LNCaP cells. The concentration of each chemotheraptuic agent was optimized to a particular concentration for each cell type that did not generate extensive cytotoxic effect from the agent alone. Under such conditions, particular chemotherapeutic agents exhibited a non-additive effect in combination with CG5757. Of the agents tested, doxorubicin and Taxol showed potential synergistic cytotoxicity with CG5757. Doxorubicin at 5 ng/ml did not generate cytotoxicity on Hep3B cells, whereas CG5757 at an MOI of 0.005 (pfu/cell) destroyed only 30% of the cells by day 7; however, co-administration of doxorubicin and CG5757 was cytotoxic to about 85% of the cells 7 days after treatment. A similar result was observed when Taxol (1 ng (ml) and CG5757 (moi 0.1) were co-administered to LNCaP cells.

These results demonstrate that the recombinant viral vectors of the present invention can provide a synergistic benefit to existing chemotherapeutic compositions and approaches.

BRIEF DESCRIPTION OF THE SEQUENCES

The following is a description of the sequences relied upon the description provided herein.

SEQ ID NO:1 is a 270 bp fragment containing sequences from the human E2F promoter.

SEQ ID NO:2 is a 239 bp fragment containing sequences from the human telomerase (TERT) promoter.

SEQ ID NO:3 is a 245 bp fragment containing sequences from the human TERT promoter.

SEQ ID NO:4 is a 2751 bp fragment containing sequences from the adenoviral vector CG5757.

SEQ ID NO:5 is a 4022 bp fragment containing the predicted sequences for the adenoviral vector OV947.

SEQ ID NO:6 is a 3207 bp fragment containing sequences from the adenoviral vector OV945.

SEQ ID NO:7 is a 4304 bp fragment containing the predicted sequences for the adenoviral vector OV1025.

SEQ ID NO:8 and 9 are primer sequences for amplifying an E2F-1 promoter.

SEQ ID NO:10 and 11 are primer sequences for amplifying a TERT promoter.

SEQ ID NO:12: is a portion of E1b that is deleted in various adenoviral vectors of the invention including CG5757 and OV947.

SEQ ID NO: 13: is a polyadenylation consensus DNA sequence.

SEQ ID NO: 14: is a polyadenylation consensus RNA sequence.

What is claimed is:

1. A recombinant viral vector comprising an adenoviral nucleic acid sequence, wherein said nucleic acid sequence comprises in sequential order: a left inverted terminal repeat (ITR), an adenoviral packaging signal, an E2F responsive promoter operatively linked to an E1a coding sequence, a telomerase (TERT) promoter operatively linked to an E1b coding sequence and a right ITR, wherein said recombinant viral vector comprises SEQ ID NO:5.

2. A pharmaceutical composition comprising the adenoviral vector of claim 1 and a pharmaceutically acceptable carrier.

3. A method of selective cytolysis of a cancer cell, comprising contacting a cell population with an effective amount of an adenoviral vector comprising an adenoviral nucleic acid sequence presented as SEQ ID NO: 5, wherein said nucleic acid sequence comprises in sequential order: a left terminal repeat (ITR), an adenoviral packaging signal, an E2F responsive promoter operatively linked to an E1a coding sequence, a telomerase (TERT) promoter operatively linked to an E1b coding sequence and a right ITR, under conditions where the adenoviral vector infects the cells of the cell population resulting in selectively cytolysis of cancer cells within said cell population.

4. The method of claim 3, further comprising a mutation or deletion in an E3 coding sequence.

5. The method of claim 3, wherein at least one E3 coding sequence has been deleted from the adenoviral nucleic acid sequence.

6. The method of claim 3, wherein an E3 coding sequence in the nucleic acid sequence codes for at least one native E3 protein.

* * * * *